US008268801B2

(12) United States Patent
Puzo et al.

(10) Patent No.: US 8,268,801 B2
(45) Date of Patent: Sep. 18, 2012

(54) SULFOGLYCOLIPID ANTIGENS, THEIR PROCESS OF PREPARATION, AND THEIR USE AGAINST TUBERCULOSIS

(75) Inventors: Germain Puzo, Auzeville Tolosane (FR); Jacques Prandi, Toulouse (FR); Martine Gilleron, Auzeville Tolosane (FR); Gennaro De Libero, Bale (CH); Julie Guiard, Toulouse (FR); Lucia Mori, Bale (CH); Samantha Paoletti, Rheinlelden (CH)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 302 days.

(21) Appl. No.: 12/524,091

(22) PCT Filed: Jan. 11, 2008

(86) PCT No.: PCT/IB2008/000053
§ 371 (c)(1),
(2), (4) Date: Feb. 17, 2010

(87) PCT Pub. No.: WO2008/090425
PCT Pub. Date: Jul. 31, 2008

(65) Prior Publication Data
US 2010/0166801 A1    Jul. 1, 2010

(30) Foreign Application Priority Data

Jan. 24, 2007  (EP) .................................. 07290097

(51) Int. Cl.
*A61K 39/04* (2006.01)
*C07H 5/10* (2006.01)
*C07H 15/06* (2006.01)
(52) U.S. Cl. .......................... 514/53; 536/18.2; 536/122
(58) Field of Classification Search ................. 536/18.2, 536/122; 514/53
See application file for complete search history.

(56) References Cited

FOREIGN PATENT DOCUMENTS
WO    WO 2004/092192 A1 *  10/2004

OTHER PUBLICATIONS

The Merck Manual,16[th] Edn, 1992, pp. 140-141.*
Wallace et al J. Chem. Soc., Comm., 1994, 320-30.*
Hamid et al Letters in Applied Microbiology, 1993, 16, 132-35.*
Written Opinion of the International Searching Authority, Sep. 6, 2008.
M.E. Hamid et al., "Antigenic glycolipids of Mycobacterium fortuitum based on trehalose acylated with 2-methyloctadec-2-enoic acid", Letters in Applied Microbiology, 1993, pp. 132-135, vol. 16, XP-002475748.
Paul A. Wallace et al., "Synthesis and Structure of 2,3-ID-O-acyl-α,α-trehalose Lipid Antigens from Mycobacterium fortuitum", Journal of the Chemical Society, Chemical Communications, 1994, pp. 329-330, No. 3, XP-008079924.

* cited by examiner

*Primary Examiner* — Shaojia Anna Jiang
*Assistant Examiner* — Ganapathy Krishnan
(74) *Attorney, Agent, or Firm* — Young & Thompson

(57) ABSTRACT

The present invention relates to compounds of the following general formula (I) their process of preparation and their use in the treatment or the prophylaxis of tuberculosis.

18 Claims, 2 Drawing Sheets

SULFOGLYCOLIPID ANTIGENS, THEIR PROCESS OF PREPARATION, AND THEIR USE AGAINST TUBERCULOSIS

The present invention relates to new sulfoglycolipid antigens, their process of preparation and their use in the treatment or the prophylaxis of tuberculosis.

Each year, tuberculosis is the estimated cause of 3 million deaths. The causative agent of this disease is a bacterium, *Mycobacterium tuberculosis*, by which one of every three people is infected worldwide. It is transmitted through the air by sneezes or coughs of infected persons. The bacterium may be harboured in an inactive state by infected persons who will never develop the disease. However, under certain conditions, such as age or depression of the immune system, the bacterium may become active and cause the onset of tuberculosis.

It seems that the mycobacterial envelope accounts for an important part of the virulence of bacteria of the *Mycobacterium* genus. Indeed, up to 40% of mycobacteria dry weight is constituted by lipids. Among those lipids, some of them seem restricted to *Mycobacterium tuberculosis*, such as sulfoglycolipids for instance (Vergne I. and Daffe M. *Frontiers in Bioscience* (1998) 3:865-876). This family of glycolipids is typified by a sulfate substituent on position 2' of a trehalose unit (i.e. α-D-glucopyranosyl-(1-1)-α'-D-glucopyranoside) (A).

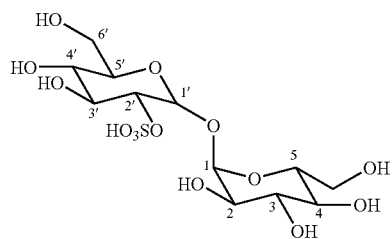

A

Members of the family differ from one another by the number, the position and the type of fatty acids substituted on the trehalose units. The fatty acids substituents notably comprise palmitic acid, stearic acid, phthioceranoic acid and hydroxyphthioceranoic acid. The latter two fatty acids are characteristic of sulfoglycolipids. The most abundant sulfoglycolipid is SL-I (Goren et al. *Biochemistry* (1976) 15:2728-2735) (B).

It has been demonstrated that SL-I was able to inhibit macrophage antimicrobial activity and to block the effects of several inflammatory agents such as LPS, IFN-γ or TNF-α on macrophages (Vergne I. and Daffe M. *Frontiers in Bioscience* (1998) 3:865-876).

At present, there are two ways of fighting tuberculosis: antibiotic therapy and vaccination.

The vaccine used for the prophylaxis of tuberculosis consists of a live attenuated bacterium of the *Mycobacterium bovis* species. It is named BCG, *Bacillus* of Calmette and Guerin, after the two scientists who first devised it, at the beginning of the 20th century. In addition to its flaw as being a live vaccine, which precludes its use in immunodepressed patients, its protection against tuberculosis is controversial. Thus, BCG protective efficacy in adults range from 0% to 80% according to varying studies, besides, it fails to protect against pulmonary tuberculosis, the most prevalent disease form in adults.

Moreover, antibiotic resistant strains of *M. tuberculosis* have been found in over 35 countries.

Hence, it is a subject of the present invention to provide a more effective way of treating and/or preventing tuberculosis.

Further immunogenic glycolipids extracted from *Mycobacterium tuberculosis* are disclosed in WO2004/092192. However, these natural products are obtainable in limited amount; additionally, they are obtained from a pathogenic strain and their preparation may be hazardous and requires specific safety installations.

It is thus highly desirable to provide further new synthetic immunogenic glycolipids obtainable in industrial scale and practicable conditions.

The invention notably provides new synthetic sulfoglycolipid antigens, which have been shown to stimulate CD1-restricted T lymphocytes in vitro.

The invention relates to compounds of the following general formula (I):

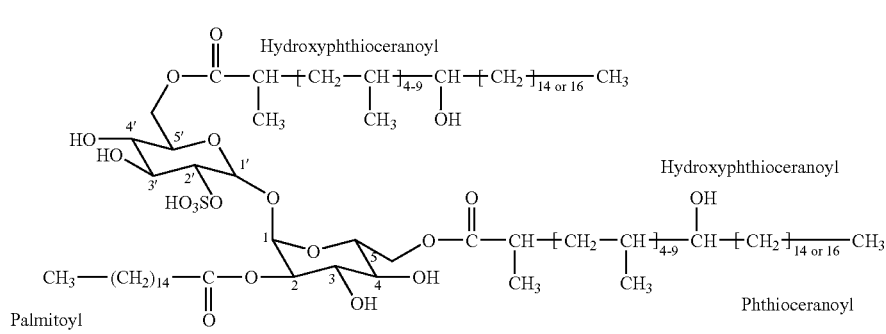

B (I)

[Structure: disaccharide with HO, HO, R³'O on one ring with OR²' bridging oxygen to second ring bearing R²O, OR³, OH, OH]

wherein $R^{2'}$, $R^{3'}$, identical or different, are independently chosen from H, $SO_3H$ or $SO_3^-/M^+$, provided that at least one of $R^{2'}$, $R^{3'}$ is $SO_3H$ or $SO_3^-/M^+$;

Preferably, $R^{2'}$ is $SO_3H$ or $SO_3^-/M^+$ and $R^{3'}$ is H.

$M^+$ is the cation of a metal, such as $Na^+$, $K^+$.

$R^2$, $R^3$, identical or different, are independently chosen from:

a) fatty acyl groups
b)

$$-\overset{O}{\underset{\|}{C}}-X,$$

where X is an unsaturated linear or ramified hydrocarbon chain optionally substituted with one or more substituents;

where at least one of $R^2$, $R^3$ is b);

and its enantiomers, diastereoisomers, mixtures thereof and pharmaceutically acceptable salts or esters.

Preferably, X is of formula (b-1):

$$-CR^i=CR^j-Y \qquad (b\text{-}1)$$

where:

Y is a saturated or unsaturated, preferably saturated, linear or ramified hydrocarbon chain optionally substituted with one or more substituents.

Preferably, Y is a saturated linear alkyl chain optionally substituted with one to ten, more preferably one to four alkyl groups, preferably methyl groups.

More preferably, the methyl groups are located at C-1, C-3, C-7 or C-9 positions of the Y chain.

More preferably, the substituted carbon atoms exhibit the (S) configuration.

$R^i$, $R^j$, identical or different, are independently chosen from H, Alkyl; preferably, $R^i$ is Methyl and $R^j$ is H.

$R^i$ and $R^j$ are such that the configuration may be (E) or (Z).

According to a preferred aspect, the b) chain is of formula (b-2):

$$\text{(b-2)}$$

[Structure with $T^2$, $T^1$, subscripts r, l, q, ending in $CH_3$]

where r is an integer chosen from 1, 2 or 3; preferably, 1;
l is an integer chosen from 0 to 10; preferably, 1, 2 or 3;
q is an integer chosen from 0 to 50; preferably, 5 to 50; more preferably 10 to 20;
provided that $l+q \geq 1$;
each $T^i$, identical or different, is independently chosen from alkyl groups; preferably, each $T^i$ is methyl.

The carbon atom to which $T^i$ is attached is asymmetric. Preferably, said carbon atom exhibits a (S) configuration.

$T^2$ is an alkyl group; preferably a Methyl.

According to another preferred aspect, $R^2$ is a) fatty acyl group and $R^3$ is b) —C=O—X as defined above.

Fatty acyl groups are derived from fatty acid groups which esterify the hydroxyl groups in position 2 or 3 of the 2'- or 3'-sulfated trehalose unit.

Fatty acid groups are aliphatic carboxylic acids which can be linear or ramified, saturated or unsaturated, unsubstituted or substituted by groups such as hydroxyl, or ketone.

Preferably, they contain from 5 to 50, preferably 15 to 50 carbon atoms, and more particularly may be selected from the group comprising:

$$-\overset{O}{\underset{\|}{C}}-(CH_2)_{\overline{6}}-CH_3$$
(octanoyl)

$$-\overset{O}{\underset{\|}{C}}-(CH_2)_{\overline{14}}-CH_3$$
(palmitoyl)

$$-\overset{O}{\underset{\|}{C}}-(CH_2)_{\overline{16}}-CH_3$$
(stearoyl)

$$-\overset{O}{\underset{\|}{C}}-(CH_2)_{\overline{18}}-CH_3$$
(arachidioyl)

$$-\overset{O}{\underset{\|}{C}}-(CH_2)_{\overline{20}}-CH_3$$
(docosanoyl)

$$-\overset{O}{\underset{\|}{C}}-(CH_2)_{\overline{22}}-CH_3$$
(tetracosanoyl)

$$-\overset{O}{\underset{\|}{C}}-CH(CH_3)-CH_2-[CH(CH_3)]_n-CH(OH)-(CH_2)_m-CH_3$$
(hydroxyphthioceranoyl)

wherein m is 14 or 16 and n is an integer from 2 to 10, $$-\overset{O}{\underset{\|}{C}}-CH(CH_3)-CH_2-[CH(CH_3)]_n-CH_2-(CH_2)_m-CH_3$$
(phthioceranoyl)

wherein m is 14 or 16 and n is an integer from 2 to 10,

The fatty acyl groups notably comprise linear and saturated fatty acyl groups such as groups according to formula —C=O—(CH$_2$)$_k$—CH$_3$ wherein k is an integer from 14 to 50.

Still more preferably, fatty acyl groups are selected from the group comprising palmitic acyl and stearic acyl.

The invention more particularly relates to compounds of formula I, wherein R$^2$ represents a fatty acyl group, preferably, a palmitic acyl group or a stearic acyl group and R$^3$ represents a (b-2) chain, namely compounds of following formula (II):

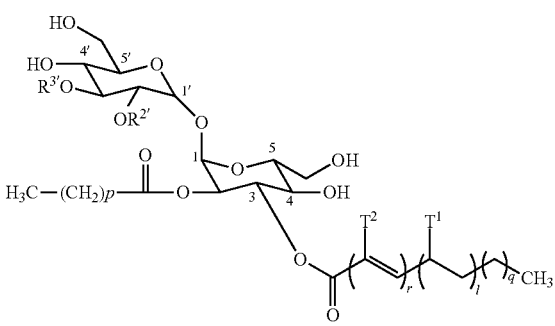

where R$^{2'}$, R$^{3'}$, p, l, q, T$^2$, T$^i$ are defined as above, or the corresponding salt thereof, and its enantiomers, diastereoisomers, mixtures thereof and pharmaceutically acceptable salts or esters.

The invention relates in particular to compounds of formula II, wherein:
l=1, q=14 and r=1;
l=2, q=14 and r=1;
l=3, q=14 and r=1;
l=4, q=14 and r=1;
l=1, q=14 and r=2;
l=2, q=14 and r=2;
l=3, q=14 and r=2;
l=4, q=14 and r=2;
l=1, q=12 and r=1;
l=2, q=12 and r=1;
l=3, q=12 and r=1;
l=4, q=12 and r=1;
l=1, q=12 and r=2;
l=2, q=12 and r=2;
l=3, q=12 and r=2;
l=4, q=12 and r=2;
l=1, q=16 and r=1;
l=2, q=16 and r=1;
l=3, q=16 and r=1;
l=4, q=16 and r=1;
l=1, q=16 and r=2;
l=2, q=16 and r=2;
l=3, q=16 and r=2; or
l=4, q=16 and r=2;
where p is 6 to 22 and T$^2$ and T$^i$ are methyl.

The invention more specifically relates to compounds of following formulae:

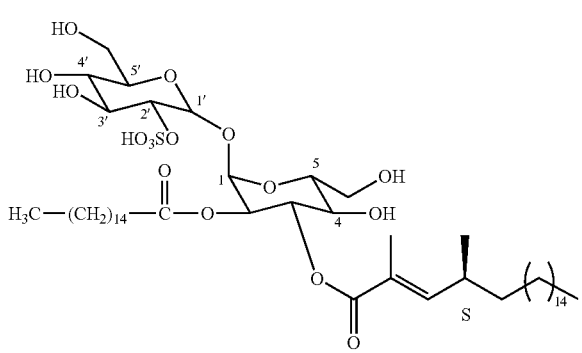

(II.1)

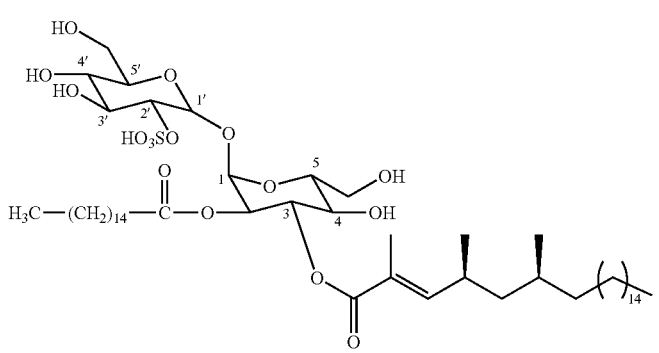

(II.2)

-continued
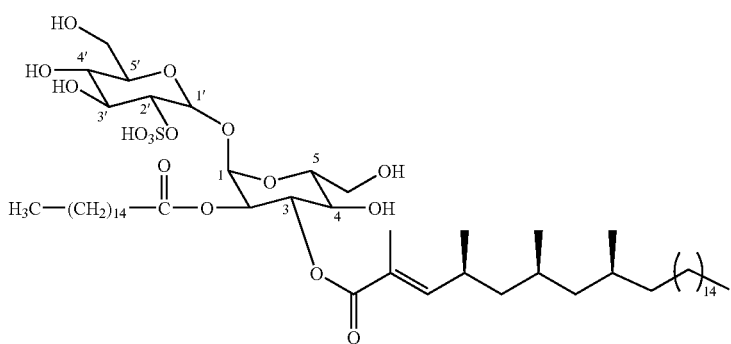
(II.3)
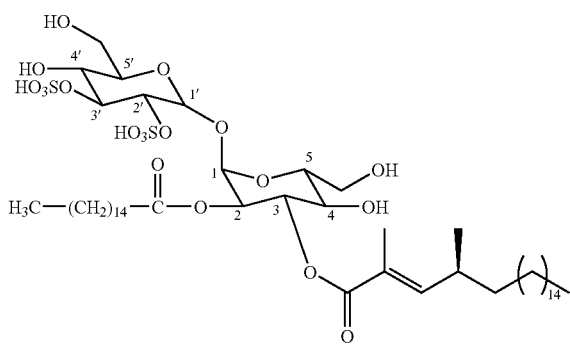
(II.4)
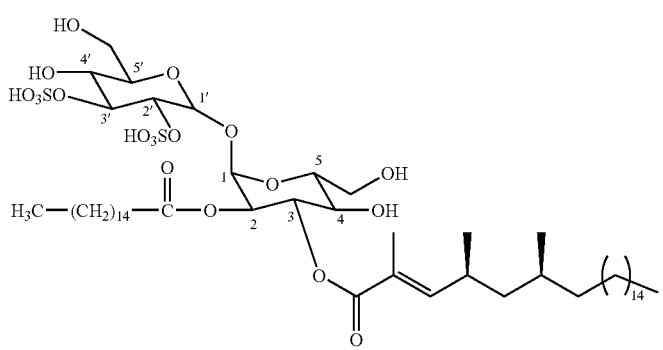
(II.5)
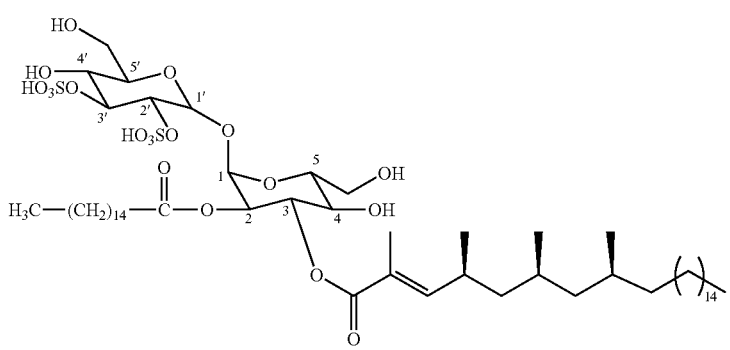
(II.6)

-continued (II.7)
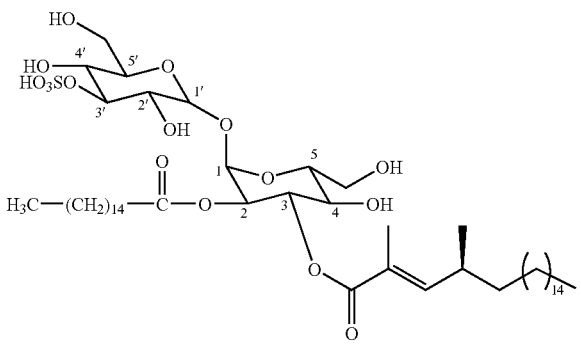

(II.8)
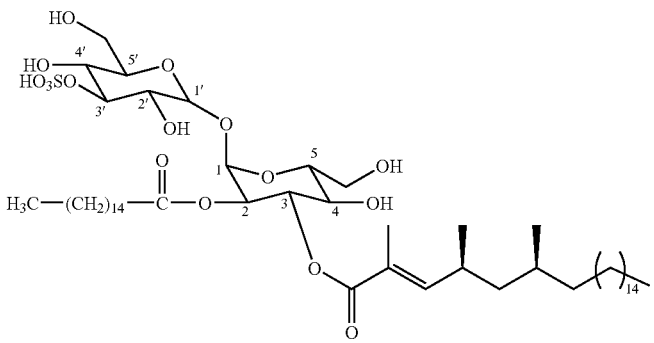

(II.9)
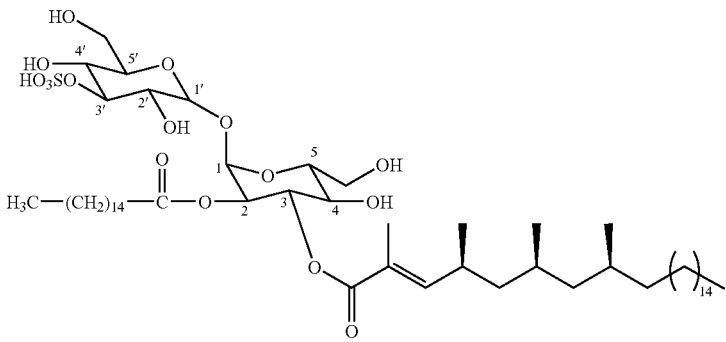

(11.10)
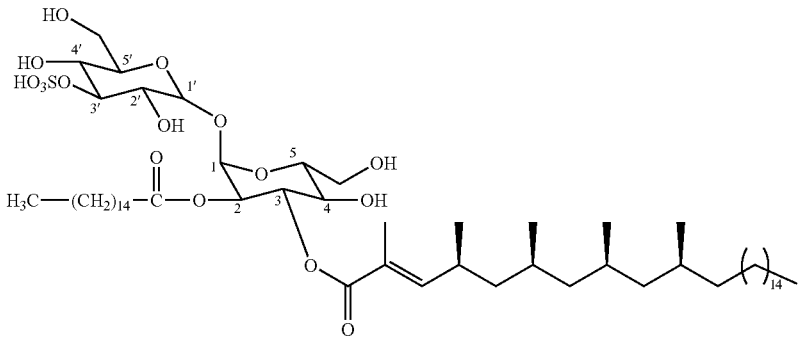

and their corresponding salts,
and its enantiomers, diastereoisomers, mixtures thereof and pharmaceutically acceptable salts or esters.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, sulfuric, sulfamic, phosphoric, nitric and the like; and the salts prepared from organic acids such as acetic, propionic, succinic, tartaric, citric, glutamic, benzoic, salicylic, toluenesulfonic, oxalic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

According to another embodiment, the invention relates to a composition comprising at least two different compounds of formula I such as defined above.

The invention also relates to a pharmaceutical composition comprising at least one compound as defined above, or a composition as defined above, in association with a pharmaceutically acceptable vehicle.

A pharmaceutically acceptable carrier comprises in particular liposomes.

The composition may also comprise vaccine adjuvants. Vaccine adjuvants for use in human individuals or animals are well known to the man skilled in the art, a list of such salts can be found for instance in "A compendium of vaccine adjuvants and excipients" 2$^{nd}$ edition, Vogel et al. Particular vaccine adjuvants notably comprise aluminum salts or M59, for example.

The invention particularly relates to a pharmaceutical composition as defined above, characterized in that it is presented in a form intended for administration by oral or injectable route.

The invention more particularly relates to a pharmaceutical composition as defined above, characterized in that it comprises one or more other products useful for the treatment or the prophylaxis of tuberculosis, such as BCG or mycobacterial proteins.

BCG stands for *Bacillus* of Calmette and Guerin, the different strains of BCG currently used for vaccination are notably described in Behr M. A. et al. *Science* (1999) 284:1520-1523.

The expression "mycobacterial proteins" refers to proteins, or fragments thereof, which are encoded by the genome of bacteria of the *Mycobacterium* genus and notably by the genome of *Mycobacterium tuberculosis*, such proteins may be advantageously recombinant. According to a preferred embodiment said mycobacterial proteins are antigens of *M. tuberculosis*.

Other products useful for the treatment or the prophylaxis of tuberculosis notably comprise immunomodulators, such as cytokines, DNA fragments encoding *M. tuberculosis* antigens, live *M. tuberculosis* deletion mutants, such as mutants in which virulence genes have been deleted, or live recombinant BCG, such as BCG expressing antigens of *M. tuberculosis*.

As used herein, tuberculosis refers to the disease caused in humans by the bacterium *Mycobacterium tuberculosis*, but also to the corresponding disease in animals.

According to another embodiment, the invention relates to products comprising:
at least one compound as defined above,
and at least one other product useful for the treatment or the prophylaxis of tuberculosis, such as BCG or mycobacterial proteins,
as a combined preparation for simultaneous, separate or sequential use in the treatment or the prophylaxis of tuberculosis.

The invention also relates to the use of at least one compound as defined above, or of an above mentioned composition, for the preparation of a medicament, notably a vaccine, intended for the treatment or the prophylaxis of tuberculosis.

Optionally, the vaccine may comprise a vaccine adjuvant such as described above.

The invention relates to the use of at least one compound as defined above, or of a composition according as defined above, as an immune reaction activator, and more particularly an inflammatory reaction activator.

By "immune reaction activator" is meant a compound which has the ability to activate components or processes of the immune reaction, in vitro or in vivo, in particular cells of the immune system, such as T lymphocytes, B lymphocytes, antigen presenting cells (APCs), such as dendritic cells or macrophages, monocytes or granulocytes.

By "inflammatory reaction activator" is meant a compound which has the ability to activate components or processes of the inflammatory reaction, in vitro or in vivo, such as diapedesis, capillary permeabilization, macrophage activation or fever onset for instance.

The invention also relates to the use of at least one compound as defined above, or of a composition as defined above, to induce the activation of T lymphocytes, notably CD1-restricted T lymphocytes. The activation can proceed in vitro or in vivo.

The activation of T lymphocytes can be assessed by several methods, such as measuring cell multiplication or cytokine production such as IFN-$\gamma$ (interferon-$\gamma$), IL-2 (interleukine-2), IL-4 (interleukine-4), or TNF-$\alpha$ (tumor necrosis factor $\alpha$), for instance.

CD1-restricted T lymphocytes are T lymphocytes which are activated by antigens presented by CD1 molecules.

The invention also relates to the use of at least one compound as defined above, or of a composition as defined above, to induce the production of IFN-$\gamma$, TNF-$\alpha$, IL-4 or granulysin.

This production induction can be done in vitro or in vivo. The production of IFN-$\gamma$, TNF-$\alpha$, IL-4 or granulysin can be measured for instance by immunoassays, such as ELISA (enzyme linked immunosorbent assay) or EIA (enzyme immunoassay).

The invention also relates to the use of at least one compound as defined above, or of an above mentioned composition, for the preparation of a composition for the diagnosis of the infection by *Mycobacterium tuberculosis*.

Tuberculosis diagnosis may prove to be difficult as the current test (tuberculin or so-called "PPD" test) can not differentiate those PPD$^+$ individuals who received BCG from those PPD$^+$ patients actually infected with latent tuberculosis.

It is thus highly desirable to provide a test specific for the infection by *Mycobacterium tuberculosis*.

This has now been made possible with the compounds of the invention.

The compounds of the invention are highly specific to *Mycobacterium tuberculosis* species. They may be used to discriminate PPD$^+$ individuals into those vaccinated with BCG and those actually infected with tuberculosis.

According to a further aspect, the present invention thus provides a method for diagnosing infection by *Mycobacterium tuberculosis* comprising the following steps:

providing a biological sample from a PPD+ individual;

contacting said sample with a compound of formula (X):

$$\text{(X)}$$

[Chemical structure showing a disaccharide with HO, HO, R³'O substituents on one sugar ring connected via O to another ring with R²'O, R²O, OH, OH, OR³ substituents]

where $R^{2'}$, $R^{3'}$, identical or different, are independently chosen from H, $SO_3H$ or $SO_3^-/M^+$, provided that at least one of $R^{2'}$, $R^{3'}$ is $SO_3H$ or $SO_3^-/M^+$;

Preferably, $R^{2'}$ is $SO_3H$ or $SO_3^-/M^+$ and $R^{3'}$ is H.

$M^+$ is the cation of a metal, such as $Na^+$, $K^+$.

$R^2$, $R^3$, identical or different, are independently chosen from:

a) fatty acyl groups b)

$$\begin{array}{c} O \\ \| \\ -C-X, \end{array}$$

where X is an unsaturated linear or ramified hydrocarbon chain optionally substituted with one or more substituents;

and its enantiomers, diastereoisomers, mixtures thereof and pharmaceutically acceptable salts or esters, assessing T lymphocytes activation; and comparing the T lymphocytes activation after and before administration of the compound.

Those individuals for which T lymphocytes are activated (ie) e.g. where IFN-γ release increased after administering a compound of the invention are infected with *Mycobacterium tuberculosis*.

The present invention also provides a kit for diagnosing tuberculosis comprising:

a compound of formula (X);

dendritic cells;

means for detecting T lymphocytes activation, e.g. release of IFN-γ.

Generally, the sulfoglycolipid activation of T cells is detected by measuring the IFN-γ released in the supernatant 48 hr after stimulation with dendritic cells and sulfoglycolipids, using any human IFN-γ ELISA detection kit (for example, purchased from BD Pharmingen).

The present invention also relates to the use of the compounds of the invention to assess the efficacy of the vaccines prepared with recombinant *Mycobacterium tuberculosis*. Vaccines have been developed using recombinant living bacteria obtained from *Mycobacterium tuberculosis* or *Mycobacterium bovis* BCG, which may e.g. overexpress a protein.

It is highly desirable to assess whether such vaccines are effective and protect the patient administered therewith. Assessment is made possible by carrying out the diagnosis method of the invention.

The present invention also relates to specific ligands to the compounds of formula (X).

As intended herein a "specific ligand" relates to any compound which can be prepared or elicited to specifically bind to a compound according to the invention.

Specific ligands notably encompass antibodies and aptamers.

The term "antibodies" relates to complete antibodies, in particular monoclonal antibodies, but also to antibody fragments which retain the ability to specifically bind to the compounds of the invention, such as the Fab, Fab', F(ab')₂, Fv or scFv fragments.

Antibody preparation is well known to the man skilled in the art. Usually, a preparation of a compound according to the invention is administered to an animal, such as a mouse, a rat, a rabbit, or a goat, by various routes, such as the intramuscular, intravascular or intraperitoneal route. Additional administration can be performed after the first administration in order to increase the production of antibodies. Antibodies are then obtained from blood drawn from the animals, or from blood derivatives such as serum or plasma, and optionally purified, for instance using affinity chromatography. Monoclonal antibodies can notably be prepared as described by Koller & Milstein (1975) *Nature* 256:495-499.

"Aptamers" may be of the peptide type or of the nucleic (e.g. desoxyribonucleic or ribonucleic) type. Nucleic aptamers can notably prepared using the well known SELEX method or as described by Ellington & Szostak (1990) *Nature* 346:818-22. Peptide aptamers can be obtained as described by Cohen et al. (1998) *Proc. Natl. Acad. Sci. USA* 95:14272-7.

General formula (X) includes formula (I) as disclosed in WO 2004/092192 incorporated herein by reference as well as compounds of formula (I) and (II) of the present invention. Preferably, the compounds of formula (X) are those of formulae (I) and (II) and their preferred embodiments as disclosed above.

According to a further object, the present invention also relates to the process of preparation of a compound of formula (I) as defined above.

The compounds and process of the present invention may be prepared in a number of ways well known to those skilled in the art. The compounds can be synthesized, for example, by application or adaptation the methods described below, or variations thereon as appreciated by the skilled artisan. The appropriate modifications and substitutions are readily apparent and well known or readily obtainable from the scientific literature to those skilled in the art.

In particular, such methods can be found in R. C. Larock, *Comprehensive Organic Transformations*, VCH publishers, 1989.

The reagents and starting materials are commercially available, or readily synthesized by well-known techniques by one of ordinary skilled in the arts.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, especially fatty acid amides, such as dimethylformamide; and ethers, such as diethyl ether and tetrahydrofuran.

The reactions can take place over a wide range of temperatures. In general, we find it convenient to carry out the reaction at a temperature of from about 0° C. to about 150° C. (more preferably from about room temperature to about 100° C.). The time required for the reaction may also vary widely, depending on many factors, notably the reaction temperature and the nature of the reagents. However, provided that the reaction is effected under the preferred conditions outlined above, a period of from about 3 hours to about 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well techniques, such as recrystallization, reprecipitation or the various chromatography techniques, notably column chromatography or preparative thin layer chromatography.

According to a further object, the present invention provides a process of preparation of a compound of formula (I) as defined above comprising the steps of:
sulfonating; and
acylating with corresponding compounds of formulae (IV) and (IV'):

R²X (IV)

R³Y (IV')

where R² and R³ are defined as in formula (I) and X and Y independently represent a halogen atom or a OH group;
a compound of formula (III):

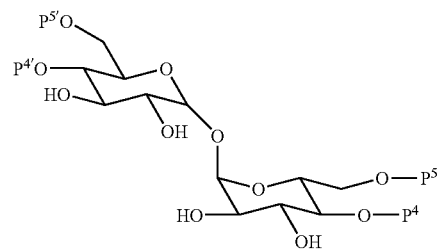

where each of $P^4$, $P^5$, $P^{4'}$, $P^{5'}$ identical or different represents H or a OH-protecting group or $P^4$ and $P^5$ and/or $P^{4'}$ and $P^{5'}$ form together a cyclic OH-protecting group.

One or two sulfonating and acylating reactions may be required.

The sulfonating and acylating steps may be carried out in any order, successively or alternatively.

One or more protecting and/or deprotecting steps may be required before and/or after the acylating and/or sulfonating steps, as appropriate.

Such protecting groups include acetals or ketal, such as

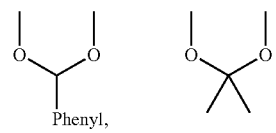
Phenyl, or bidentate protecting groups such as

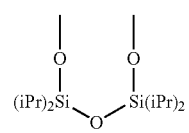

The process of the invention comprises the further step of hydrolyzing said protecting groups. This reaction is usually carried out in acid conditions.

Said sulfonation reaction is generally carried out with any suitable sulfonating agent, such as the pyridine-sulfur trioxide complex or trimethylamine-sulfur trioxide complex.

The two required acylations may be carried out in one or two steps. The acylation step(s) is/are usually conducted with coupling agents such as DMAP and/or DCC.

The process of the invention may also comprise the final step of isolating the desired compound.

A representative process of the invention is illustrated in the following scheme:

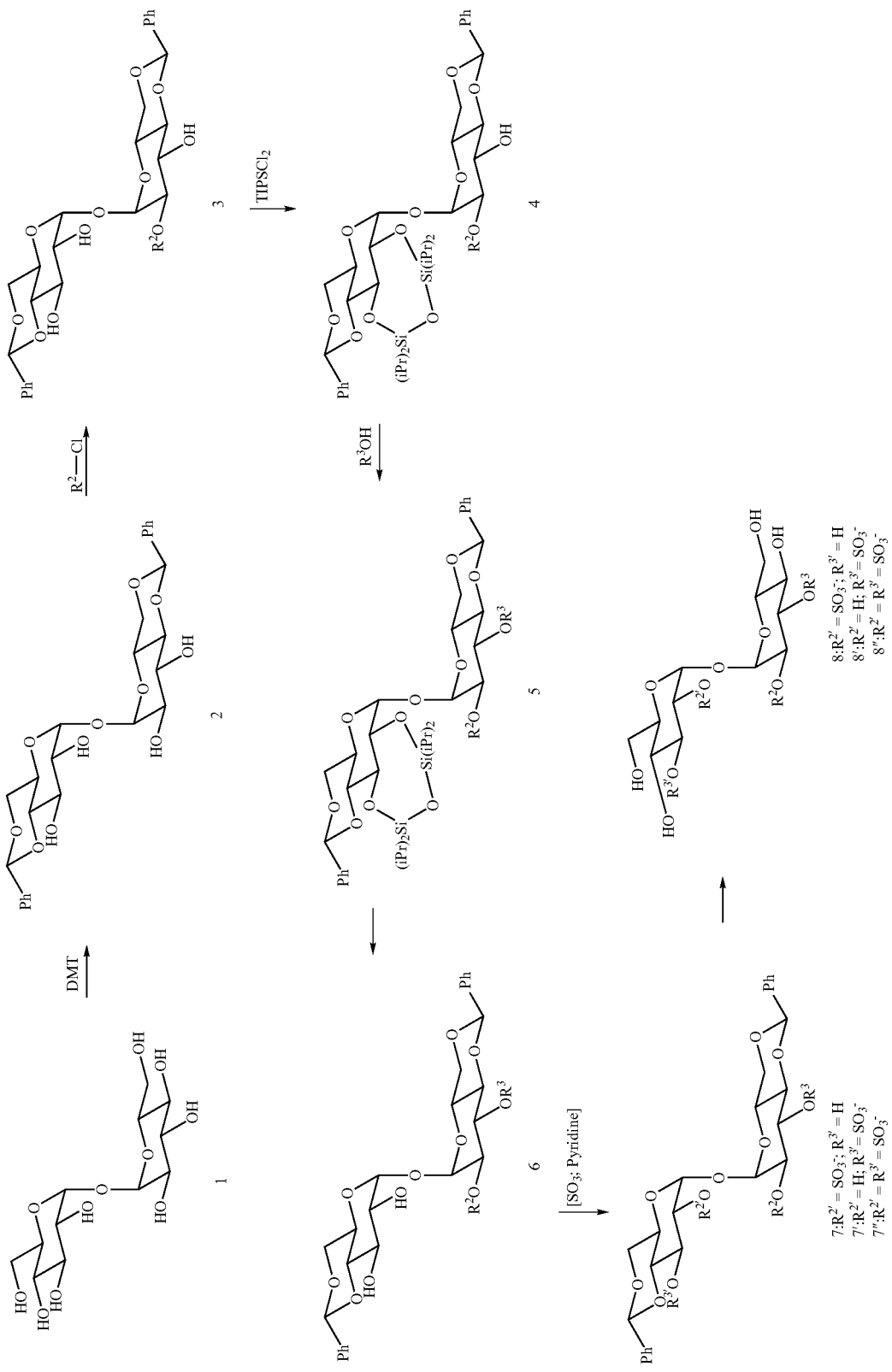

The 2', 3' bi-sulfonated compound (7") may be obtained by using excess of the sulfonating reagent. The 3'-sulfonated compound (7') is obtained as a byproduct of the sulfonating reaction; usually, the selectivity of the sulfonating reaction is about 5/1. Compounds 7, 7' and 7" are separated by chromatography.

The compound of formula (IV) is generally commercially available. Preferably, when $R^3$ represents the b) chain as defined above, the compounds of formula (IV') may be prepared by application or adaptation of the following illustrative scheme:

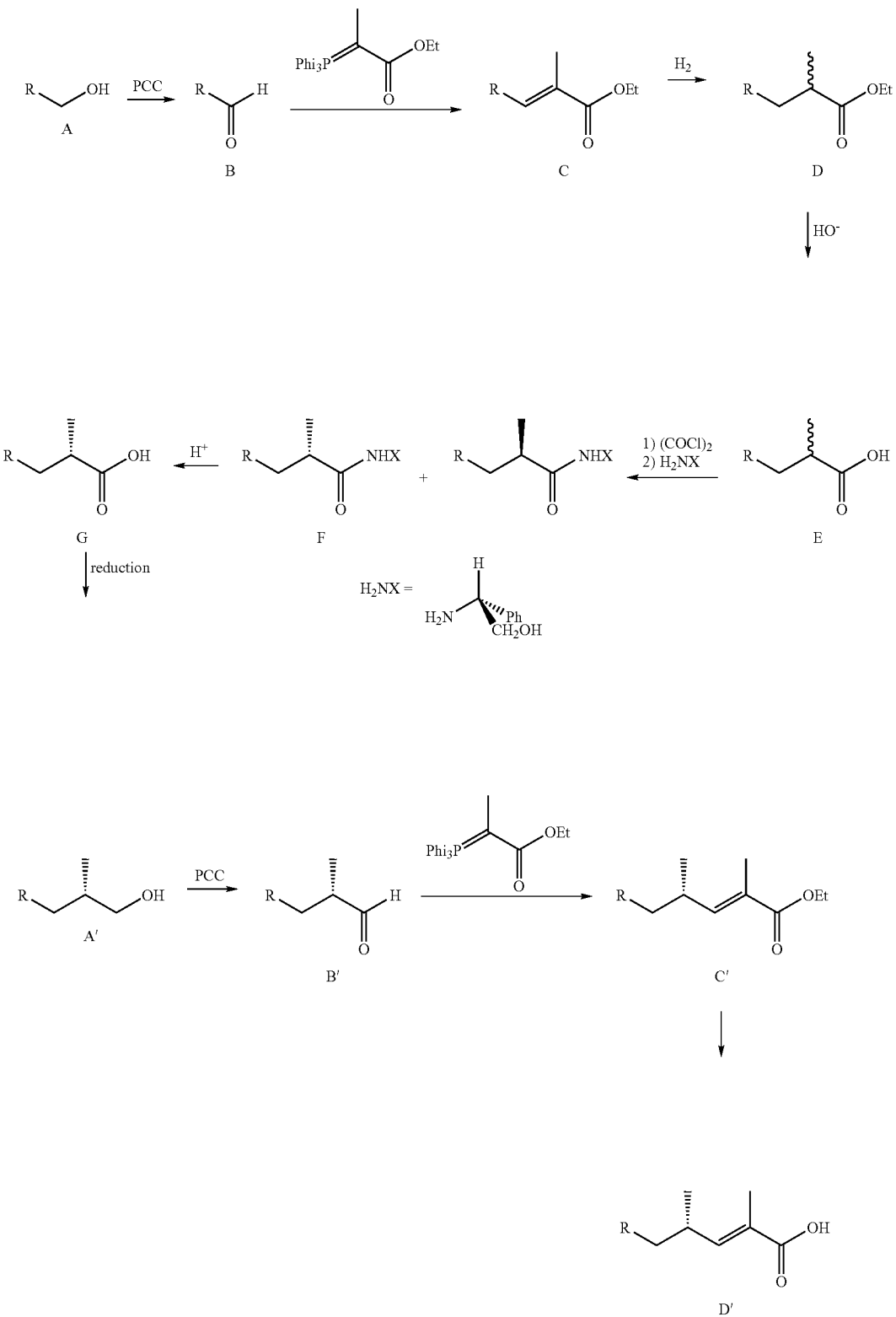

wherein
R represents the corresponding optionally substituted unsaturated linear or ramified hydrocarbon chain so that

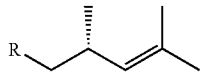

corresponds to X.

More precisely, starting from commercially available A, steps are carried out up to G which then comprises an additional methyl group with the required (S) stereochemistry. G is then reduced into reduced A' leading to desired B', then C' which in turn is saponified to lead to the desired compound of formula (IV').

In particular, the compound of formula $R^3Y$ (IV') having the following formula (IV'-a):

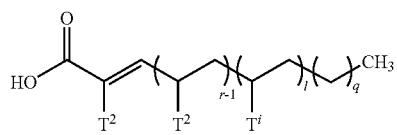

(IV'-a)

is obtained from corresponding compound of formula (V'):

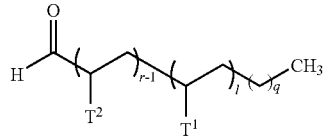

(V')

by a Wittig reaction, by using a compound of formula (VI) followed by a saponification:

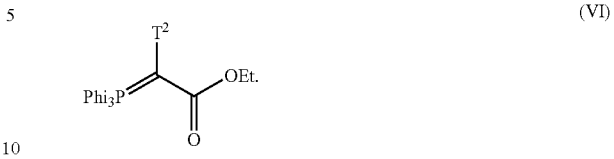

(VI)

The above process of preparation of compounds of formula (IV') is particularly advantageous in that it leads to compounds with the desired stereochemistry.

The process may be carried out by applying or adapting the experimental conditions and/or starting products given in the examples.

BRIEF DESCRIPTION OF THE DRAWING

FIGS. 1 and 2 represent the amount of IFN-γ (in pg/mL, vertical axis) produced by T cell clone Z4B27 in response to stimulation (horizontal axis) by the compounds of the invention comparative compounds.

EXAMPLES

Example 1

Figure 1:
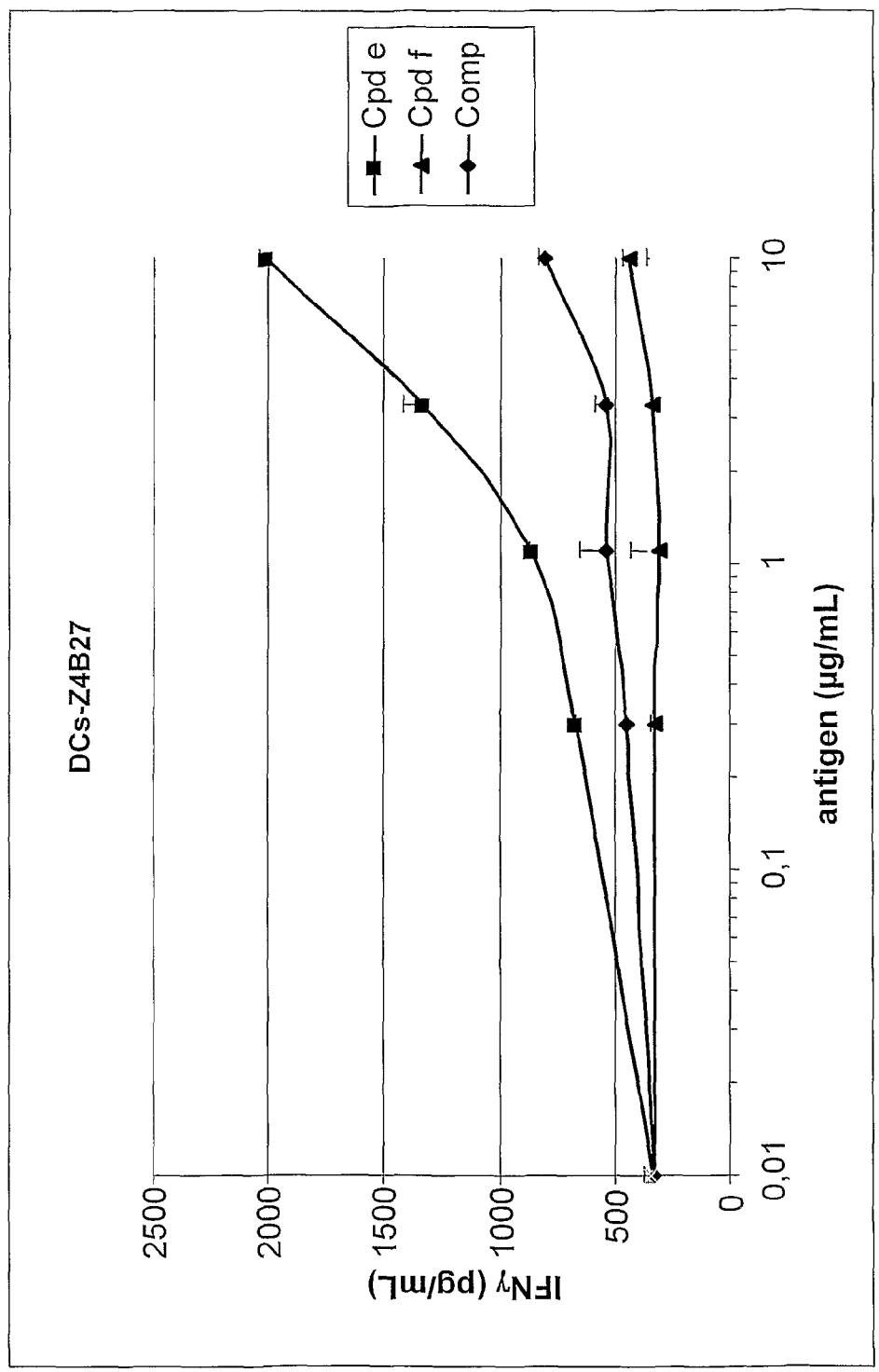
FIG. 1 and FIG. 2

Synthesis of the Compounds of the Invention

A. Synthesis of Sulfolipids

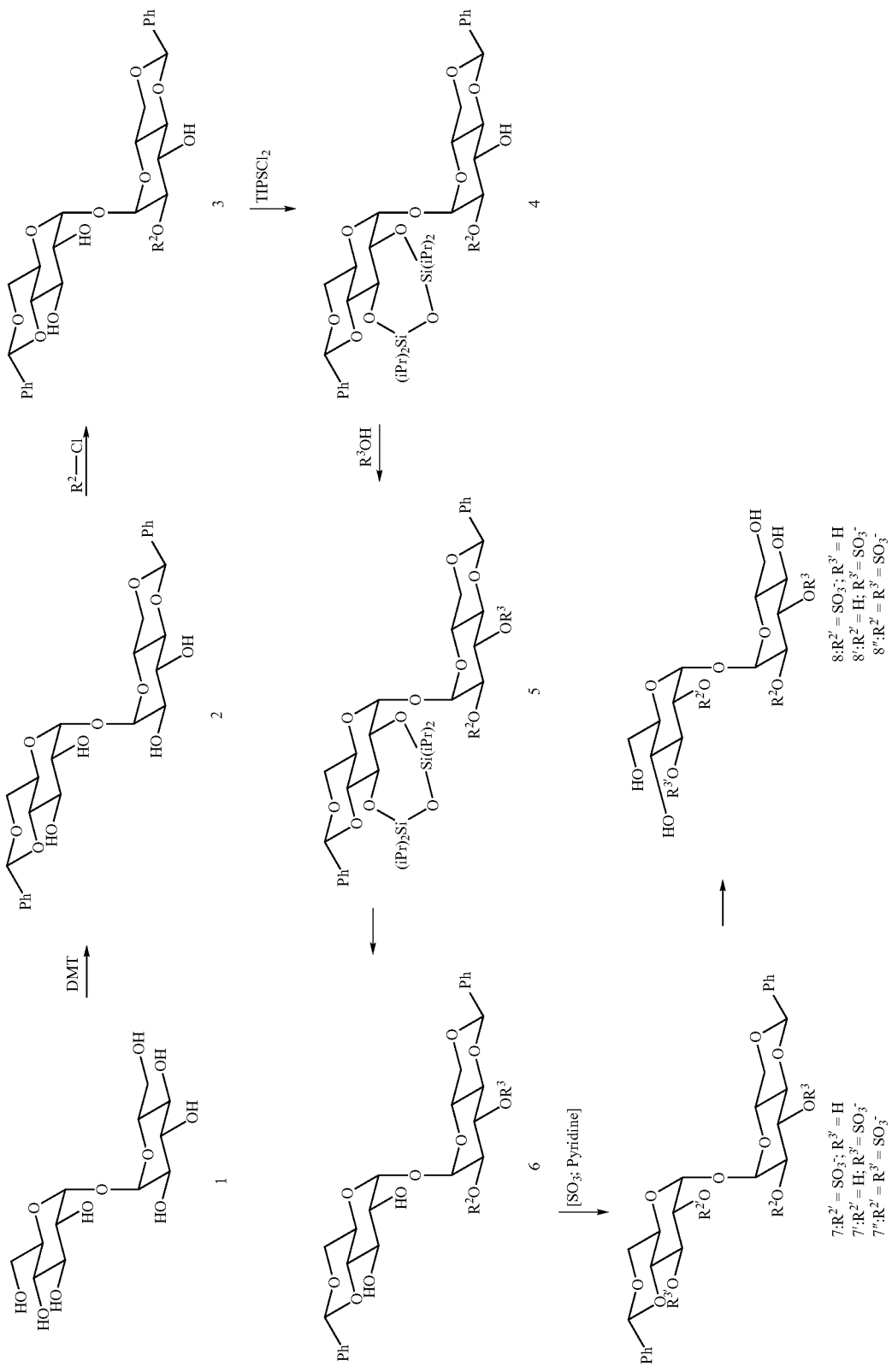

1. Benzylidenation of α,α-trehalose

α,α-Trehalose dihydrate (1 eq.) was dehydrated by boiling in absolute ethanol (0.4 M) under reflux for 30 min. The dry residue 1 was then suspended in dry N,N-dimethylformamide (DMF, 0.4 M), and α,α-dimethoxytoluene (DMT, 2 eq.) was added, together with 10-camphorsulfonic acid (CSA, 0.05 eq.). The mixture was heated (60° C.) during 1 h on a rotary evaporator with a light vacuum to eliminate the methanol. More DMT (0.25 eq.) and CSA (0.01 eq.) were then added and the mixture was attached again on the rotary evaporator. At the end of the reaction, DMF was evaporated. The mixture was stirred overnight in an aqueous sodium hydrogencarbonate solution (5%) to give crystalline diacetal 2. The product was recrystallized by dissolution in boiling ethanol, addition of hot water, and slow cooling. Finally, the white crystals of 2 were filtered, washed with water and ether petroleum and dried (84%).

2. Acylation of Position 2

A suspension of diacetal 2 (1 eq.), 4-dimethylaminopyridine (DMAP, 1 eq.) and acyl chloride (1.3 eq) in dry pyridine (0.6 M) was boiled under reflux during 25 h. The monoacylated product 3 was obtained in 45% yield.

3. Silylation of Positions 2' and 3'

To an ice-cooled solution of 3 (1 eq.) in pyridine (0.1 M) was added 1,3-dichloro-1,1,3,3-tetraisopropyldisiloxane (1.2 eq.). After stirring for 2 days at room temperature, the mixture was poured into ice-water and the product extracted with ethyl acetate. Purification by flash chromatography and gave product 4 as a syrup in 58% yield.

4. Acylation of Position 3

Compound 4 (1.5 eq.) was treated during 15 min under microwaves with the acid $R^3OH$ (obtained from part B) (1 eq.), DMAP (1 eq.) and DCC (1.5 eq.) in dry toluene (0.1 M of acid). At the end, the solvent was evaporated and the diacylated product 5 was purified by flash chromatography. The yield of the reaction in highly dependent on the structure of the acid used (25-60%).

5. Desilylation

Compound 5 (1 eq.) was heated at 40° C. with a solution of $Bu_4NF/THF$ (1 M, acidified with trifluoroacetic acid to have pH≈6, 40 eq.) during 24 h. The crystalline product 6 was obtained in 90% yield.

6. Sulfatation

To a solution of 6 (1 eq.) in pyridine (0.06 M) was added a solution of pyridine-sulfur trioxide complex in DMF (0.5 M, 3 eq.) and the mixture was stirred at room temperature. After 2 days, the mixture was evaporated and the residue chromatographed on silica gel to give 7 (62%), its 3'-sulfate isomer 7' and the 2',3'-disulfated compound 7".

7. Hydrolysis of the Acetals

The dibenzylidene derivative 7, 7' or 7" was treated with a solution of chloroform/methanol/1.7% $H_2SO_4$ (60/40/8) for 2 days at room temperature. The reaction mixture was made neutral with a solution of $NaHCO_3$. This deprotection afforded quantitatively the corresponding diacylated sulfoglycolipid 8, 8' or 8".

B. Synthesis of Acids

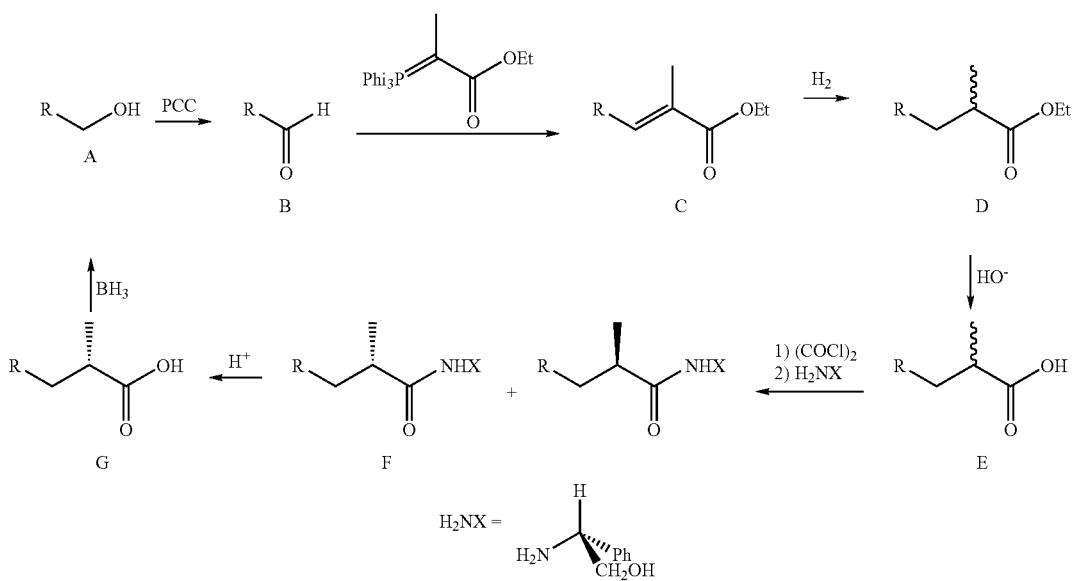

1. Oxidation of Alcohol

Alcohol A (1 eq.) was added to a rapidly stirred suspension of pyridinium chlorochromate (2 eq.) and sodium acetate (5 eq.) in dry dichloromethane (0.4 M of A) under nitrogen at room temperature. After stirring during 1.5 h diethyl ether was added and the mixture was filtered. The crude product B was not purified further.

2. Wittig Reaction

To a solution of B (1 eq.) in dry dichloromethane (0.6 M) was added 1-carboethoxyethylidene triphenylphosphorane (1.2 eq.). The mixture was then stirred overnight at room temperature and furnished the ester C. The yield of the 2 steps from A was 87%.

3. Hydrogenation

The conjugated ester C (1 eq.) was hydrogenolyzed in ethyl acetate (0.4 M) using 10% palladium on carbon as catalyst. The saturated ester D was obtained in 77% as a 1/1 enantiomeric (diastereoisomeric) mixture on the C-2 position.

4. Saponification

Ester D (1 eq.) was heated overnight at 110° C. in a solution of potassium hydroxyde (12 eq.) in water/ethanol 2/3 (0.2 M).

This reaction afforded quantitavely the corresponding acid E as a racemic (1/1 diastereoisomeric) mixture on the C-2 position.

5. Amidation

Acid E (1 eq.) was heated under reflux with oxalyl chloride (10 eq.) for 1 h. Excess reagent was removed under reduced pressure. Dry dichloromethane (0.4 M) and DMAP (1.2 eq.) followed by (R)-2-phenylglycinol (1.1 eq.) were added to the crude acyl chloride and the reaction mixture wax stirred at room temperature overnight. A flash chromatography permitted the separation of the diastereoisomers. The 2S diastereisomer F was the less polar compound and was isolated in 36% yield.

6. Acid Hydrolysis

Amide F (1 eq.) was refluxed overnight in a solution of sulphuric acid (3 N) in a 1/1 dioxan/water mixture (0.02 M) to quantitatively liberate the 2S-acid G.

7. Reduction

Acid G (1 eq.) was dissolved in a solution of $BH_3$ in THF (1 M, 1.7 eq.) and this mixture was stirred overnight at room temperature. Ethanol was added, then 80% aqueous acetic acid and the mixture was made neutral with $NaHCO_3$. The alcohol was obtained quantitatively in pure form.

The whole sequence of reaction was repeated for the introduction of other methyl ramifications on the fatty acid chain.

Unsaturated acids were obtained by saponification as above of the unsaturated esters C.

The following acids were obtained:

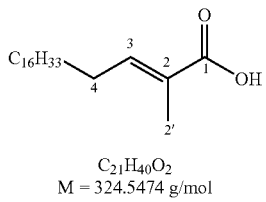

(2E)-2-methyleicos-2-enoic acid

White Crystals

RMN $^1$H (250 MHz CDCl$_3$)

δ=0.88 ppm (t, H-t, $^3$J=6.5 Hz); δ=1-1.7 ppm (m, H aliphatic); δ=1.84 ppm (d, H-2', d, $^4$J$_{2'-3}$=1.5 Hz); δ=2.19 ppm (quad, H-4, $^3$J$_{4-3}$=$^3$J$_{4-5}$=7 Hz); δ=6.9 ppm (tq, H-3, $^3$J$_{3-4}$=7 Hz and $^4$J$_{3-2'}$=1.5 Hz)

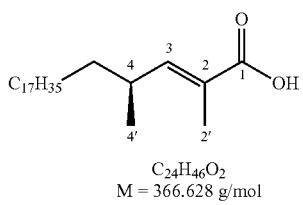

(2E,4S)-2,4-dimethyldocos-2-enoic acid

White Crystals

RMN $^1$H (250 MHz, CDCl$_3$)

δ=0.87 ppm (t, H-t, $^3$J=6.5 Hz); δ=1.0 ppm (d, H-4', $^3$J$_{4'-4}$=6.5 Hz); δ=1.1-1.6 ppm (m, H aliphatic); δ=1.84 ppm (d, H-2', d, $^4$J$_{2'-3}$=1.5 Hz); δ=2.5 ppm (m, H-4); δ=6.65 ppm (dquad, H-3, $^3$J$_{3-4}$=10 Hz and $^4$J$_{3-2'}$=1.5 Hz)

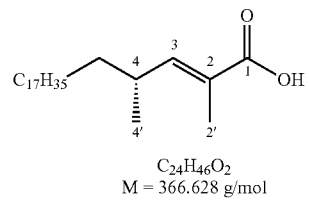

(2E,4R)-2,4-dimethyldocos-2-enoic acid

White Crystals

RMN $^1$H (250 MHz, CDCl$_3$)

δ=0.88 ppm (t, H-t, $^3$J=6.5 Hz); δ=1.01 ppm (d, H-4', $^3$J$_{4'-4}$=6.5 Hz); δ=1.1-1.5 ppm (m, H aliphatic); δ=1.85 ppm (d, H-2', d, $^4$J$_{2'-3}$=1.5 Hz); δ=2.5 ppm (m, H-4); δ=6.67 ppm (dquad, H-3, $^3$J$_{3-4}$=10 Hz and $^4$J$_{3-2'}$=1.5 Hz);

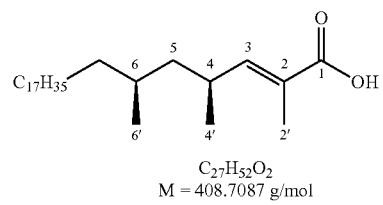

(2E,4S,6S)-2,4,6-trimethyltetracos-2-enoic acid
(Phtienoic acid)

White Crystals

[α]$_D^{25}$=+13.8 (chloroform)

RMN $^1$H (250 MHz, CDCl$_3$)

δ=0.82 ppm (d, H-6', $^3$J$_{6'-6}$=6.5 Hz); δ=0.88 ppm (t, H-t, $^3$J=7 Hz); δ=0.99 ppm (d, H-4', $^3$J$_{4'-4}$=6.5 Hz); δ=1.05-1.4 ppm (m, H aliphatic); δ=1.85 ppm (d, H-2', $^4$J$_{2'-3}$=1.5 Hz); δ=2.6 ppm (m, H-4); δ=6.66 ppm (d, H-3, $^3$J$_{3-4}$=10 Hz, $^4$J$_{3-2'}$=1.5 Hz)

RMN $^{13}$C (250 MHz, CDCl$_3$)

δ=12.1 ppm, C-6'; δ=14.1 ppm, C-t; δ=19-32 ppm, C aliphatic δ=37.6 ppm, C-2'; δ=44.4 ppm, C-5; δ=125 ppm, C-2; δ=151.2 ppm, C-3.

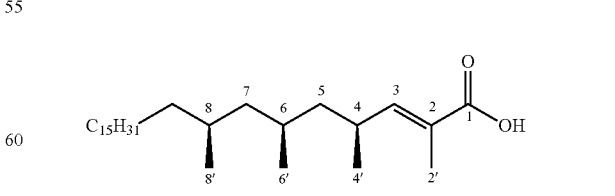

(4S,6S,8S)-2,4,6,8-tetramethyltetracos-2-enoic acid

Colorless Oil $[\alpha]_D^{25}$=+15 (chloroform)

RMN $^1$H (300 MHz, CDCl$_3$)

δ=0.83 ppm (d, H-8', $^3$J$_{8'-8}$=6.3 Hz); δ=0.85 ppm (d, H-6', $^3$J$_{6'-6}$=6.3 Hz); δ=0.9 ppm (t, H-t, $^3$J=6.6 Hz); δ=1.01 ppm (d, H-4', $^3$J$_{4'-4}$=6.6 Hz); δ=1.1-1.5 ppm (m, H aliphatic); δ=1.88 ppm (s, H-2'); δ=2.67 ppm (m, H-4); δ=6.69 ppm (d, H-3, $^3$J$_{3-4}$=10.2 Hz)

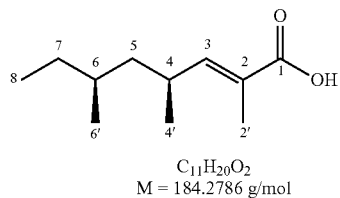

C$_{11}$H$_{20}$O$_2$
M = 184.2786 g/mol (4S,6S)-2,4,6-trimethyloct-2-enoic acid Colorless Oil $[\alpha]_D^{25}$=+53.2 (chloroform)

RMN $^1$H (250 MHz, CDCl$_3$)

δ=0.86 ppm (d, H-6', $^3$J$_{6'-6}$=5.5 Hz); δ=0.88 ppm (t, H-8, $^3$J$_{8-7}$=7 Hz); δ=1.03 ppm (d, H-4', $^3$J$_{4'-4}$=6.6 Hz); δ=1.1-1.5 ppm (m, H-5, H-6, H-7); δ=1.89 ppm (s, H-2'); δ=2.67 ppm (m, H-4); δ=6.7 ppm (d, H-3, $^3$J$_{3-4}$=10 Hz);

RMN $^{13}$C (300 MHz, CDCl$_3$)

δ=11.2 ppm, C-8; δ=12.1 ppm, C-2'; δ=19.0 ppm, C-6'; δ=20.4 ppm, C-4' δ=30.0 ppm, C-7; δ=31.1 ppm, C-4; δ=32.3 ppm, C-6; δ=44.1 ppm, C-5 δ=125.5 ppm, C-2; δ=151.1 ppm, C-3; δ=174.1 ppm, C-1.

The following compounds of the invention were prepared by applying the above procedures.

Compound a:

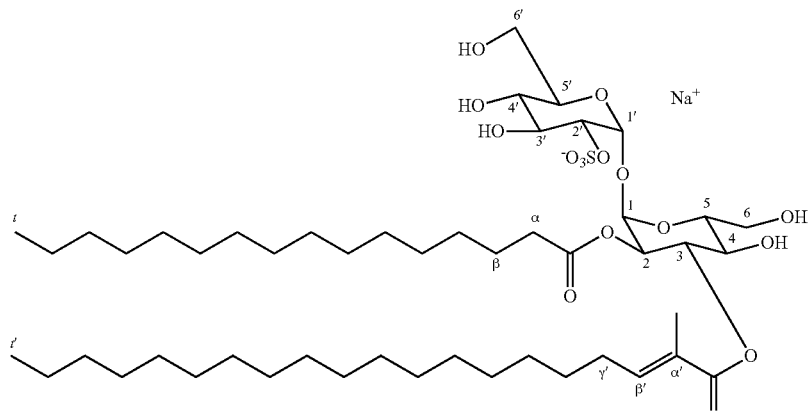

C$_{49}$H$_{89}$O$_{16}$ S Na
M = 989.2911 g/mol

2-O-Hexadecanoyl-3-O-(2-methyleicos-2-enoyl)-2'-O-sulfate-α,α'-D-trehalose

RMN $^1$H (250 MHz, CDCl$_3$/MeOD 4/1)

$\delta$=0.89 ppm (t, 3H-t, 3H-t', $^3$J=7 Hz); $\delta$=1-1.6 ppm (m, H aliphatic); $\delta$=1.81 ppm (d, (CH$_3$)$_{\alpha'}$, $^4$J=1 Hz); $\delta$=2.2 ppm (m, 2H-α, 2H-γ'); $\delta$=3.3-4.7 ppm (m, H-2', H-3', H-4, H-4', H-5, H-5', H-6$_{ax}$, H-6'$_{ax}$, H-6$_{eq}$, H-6'$_{eq}$); $\delta$=4.95 ppm (dd, H-2, $^3$J$_{2-1}$=4 Hz and $^3$J$_{2-3}$=10 Hz); $\delta$=5.29 ppm (d, H-1, $^3$J$_{1-2}$=4 Hz); $\delta$=5.45 ppm (t, H-3, $^3$J$_{3-4}$=$^3$J$_{3-2}$=10 Hz); $\delta$=5.52 ppm (d, H-1', $^3$J$_{1'-2'}$=4 Hz); $\delta$=6.8 ppm (tquad, H-β', $^2$J$_{\beta'-\gamma'}$=7.5 Hz, $^4$J=1 Hz).

MALDI-Tof (negative mode): M/Z=965.75

Compound b:

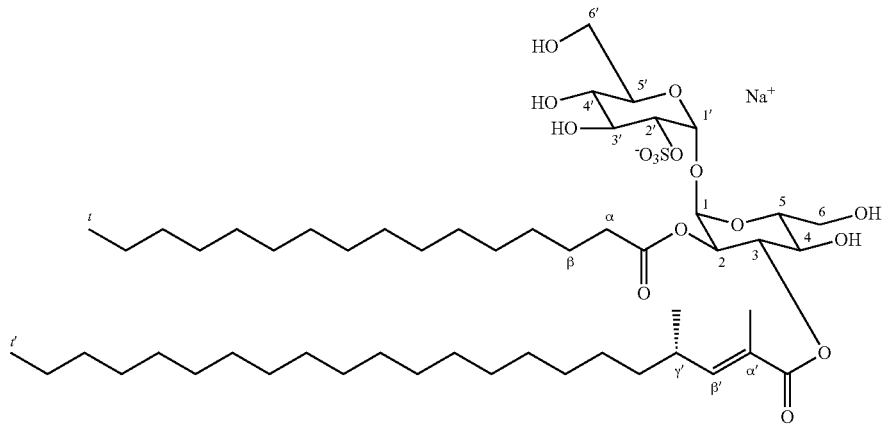

C$_{52}$H$_{95}$O$_{16}$ S Na
M = 1031.3717 g/mol

3-O-(2,4S-Dimethyldocos-2-enoyl)-2-O-hexadecanoyl-2'-O-sulfate-α,α'-D-trehalose RMN $^1$H (250 MHz, CDCl$_3$/MeOD 4/1)

$\delta$=0.9 ppm (t, 3H-t, 3H-t', $^3$J=6.5 Hz); $\delta$=0.99 ppm (d, (CH$_3$)$_{\gamma'}$, $^3$J=6.5 Hz); $\delta$=1.1-1.6 ppm (m, H aliphatic); $\delta$=1.82 ppm (d, (CH$_3$)$_{\alpha'}$, $^4$J=1 Hz); $\delta$=2.22 ppm (t, 2H-α, $^3$J=7 Hz); $\delta$=2.46 ppm (m, H-γ'); $\delta$=3.4-4.4 ppm (m, H-2', H-3', H-4, H-4', H-5, H-5', H-6$_{ax}$, H-6'$_{ax}$, H-6$_{eq}$, H-6'$_{eq}$); $\delta$=4.87 ppm (dd, H-2, $^3$J$_{2-1}$=4 Hz and $^3$J$_{2-3}$=10 Hz); $\delta$=5.29 ppm (d, H-1, $^3$J$_{1-2}$=4 Hz); $\delta$=5.44 ppm (t, H-3, $^3$J$_{3-4}$=$^3$J$_{3-2}$=10 Hz); $\delta$=5.51 ppm (d, H-1', $^3$J$_{1'-2'}$=4 Hz); $\delta$=6.57 ppm (dquad, H-β', $_3$J$_{\beta'-\gamma'}$=10 Hz, $^4$J=1 Hz).

MALDI-Tof (negative mode): M/Z=1007.59

Compound c:

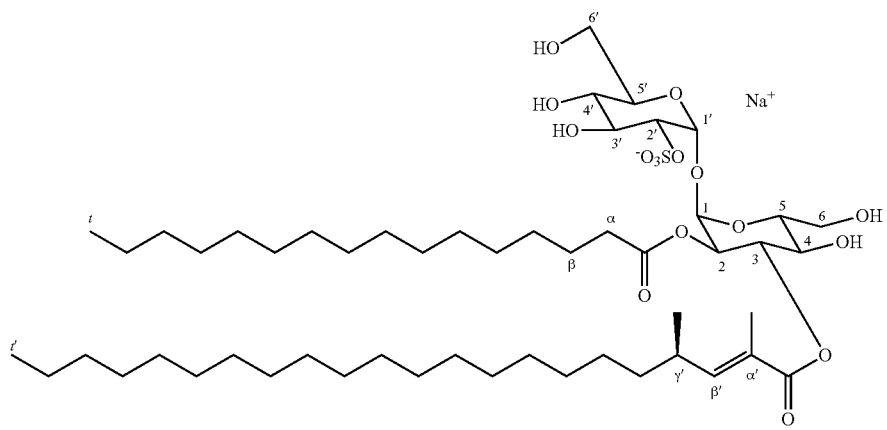

C$_{52}$H$_{95}$O$_{16}$ S Na
M = 1031.3717 g/mol

3-O-(2,4S-Dimethyldocos-2-enoyl)-2-O-hexadecanoyl-2'-O-sulfate-α,α'-D-trehalose RMN $^1$H (250 MHz, CDCl$_3$/MeOD 4/1)

δ=0.89 ppm (t, 3H-t, 3H-t', $^3$J=6.5 Hz); δ=0.99 ppm (d, (CH$_3$)$_{γ'}$, $^3$J=6.5 Hz); δ=1-1.6 ppm (m, H aliphatic); δ=1.82 ppm (d, (CH$_3$)$_{α'}$, $^4$J=1 Hz); δ=2.21 ppm (t, 2H-α, $^3$J=7.5 Hz); δ=2.5 ppm (m, H-γ'); δ=3.3-4.7 ppm (m, H-2', H-3', H-4, H-4', H-5, H-5', H-6$_{ax}$, H-6'$_{ax}$, H-6$_{éq}$, H-6'$_{éq}$); δ=4.95 ppm (dd, H-2, $^3$J$_{2-1}$=4 Hz and $^3$J$_{2-3}$=10 Hz); δ=5.29 ppm (d, H-1, $^3$J$_{1-2}$=4 Hz); δ=5.45 ppm (t, H-3, $^3$J$_{3-4}$=$^3$J$_{3-2}$=10 Hz); δ=5.52 ppm (d, H-1', $^3$J$_{1'-2'}$=4 Hz); δ=6.57 ppm (dquad, H-β', $^3$J$_{β'-γ'}$=10 Hz, $^4$J=1 Hz).

MALDI-Tof (negative mode): M/Z=1007.49

Compound d:

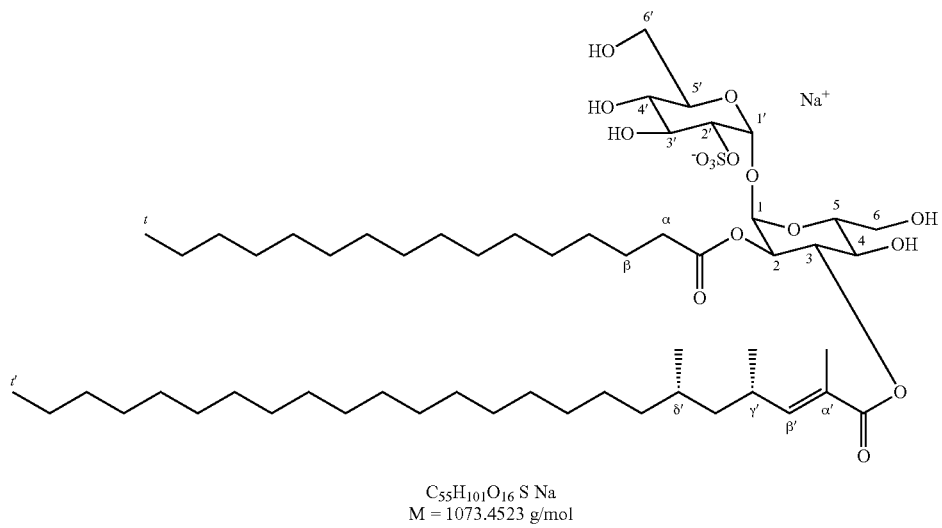

C$_{55}$H$_{101}$O$_{16}$ S Na
M = 1073.4523 g/mol

2-O-Hexadecanoyl-2'-O-sulfate-3-O-[(E)-(4S,6S)-2,4,6-trimethyltetracos-2-enoyl]-α,α'-D-trehalose RMN $^1$H (500 MHz, CDCl$_3$/MeOD 4/1)

δ=0.86 ppm (d, (CH$_3$)$_δ'$, $^3$J=6.5 Hz); δ=0.88 ppm (t, 3H-t, 3H-t', $^3$J=7 Hz); δ=0.97 ppm (d, (CH$_3$)$_{γ'}$, $^3$J=6.5 Hz); δ=1-1.6 ppm (m, H aliphatic); δ=1.82 ppm (d, (CH$_3$)$_{α'}$, $^4$J=1.5 Hz); δ=2.22 and 2.26 ppm (2quint, 2H-α, $^3$J$_{α-β}$=8 Hz, $^2$J=16 Hz); δ=2.62 ppm (m, H-γ'); δ=3.5-3.8 ppm (m, H-4, H-4', H-5', H-6, 2H-6'); δ=3.94 ppm (t, H-3', $^3$J$_{3'-2'}$=$^3$J$_{3'-4'}$=10 Hz); δ=3.97 ppm (dd, H-6, $^2$J=12 Hz, $^3$J$_{6-5}$=3 Hz); δ=4.23 ppm (m, H-2', H-5); δ=4.97 ppm (dd, H-2, $^3$J$_{2-1}$=3.6 Hz and $^3$J$_{2-3}$=10 Hz); δ=5.25 ppm (d, H-1, $^3$J$_{1-2}$=3.6 Hz); δ=5.43 ppm (t, H-3, $^3$J$_{3-4}$=$^3$J$_{3-2}$=10 Hz); δ=5.46 ppm (d, H-1', $^3$J$_{1'-2'}$=3.6 Hz); δ=6.54 ppm (dquad, H-β', $^3$J$_{β'-γ'}$=10 Hz, $^4$J=1.5 Hz)

MALDI-Tof (negative mode): M/Z=1049.47

Compound e:

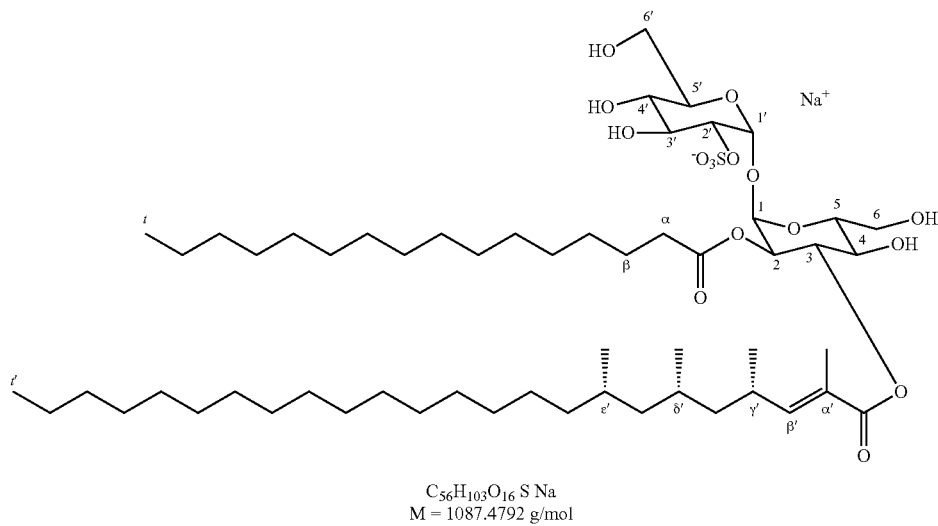

$C_{56}H_{103}O_{16}SNa$
M = 1087.4792 g/mol

2'-O-Sulfate-2-O-hexadecanoyl-3-O-[(4S,6S,8S)-2,4,6,8-tetramethyltetracos-2-enoyl]-α,α'-D-trehalose RMN $^1$H (250 MHz, CDCl$_3$/MeOD 4/1)

δ=0.89 ppm (t, 3H-t, 3H-t', $^3$J=6.5 Hz); δ=0.82; 0.84 and 0.97 ppm (3d, (CH$_3$)$_{γ'}$, (CH$_3$)$_{δ'}$, (CH$_3$)$_{ε'}$); δ=1-1.6 ppm (m, H aliphatic); δ=1.84 ppm (d, (CH$_3$)$_{α'}$, $^4$J=1 Hz); δ=2.24 ppm (m, 2H-α); δ=2.6 ppm (m, H-γ'); δ=3-4.5 ppm (m, H-2', H-3', H-4, H-4', H-5, H-5', 2H-6, 2H-6'); δ=4.96 ppm (dd, H-2, $^3$J$_{2-1}$=4 Hz and $^3$J$_{2-3}$=10 Hz); δ=5.27 ppm (d, H-1, $^3$J$_{1-2}$=4 Hz); δ=5.43 ppm (t, H-3, $^3$J$_{3-4}$=$^3$J$_{3-2}$=10 Hz); δ=5.48 ppm (d, H-1', $^3$J$_{1'-2'}$=4 Hz); δ=6.54 ppm (dq, H-β', $^3$J$_{β'-γ'}$=10.2 Hz, $^4$J=1 Hz).

MALDI-Tof (negative mode): M/Z=1063.66

Compound f:

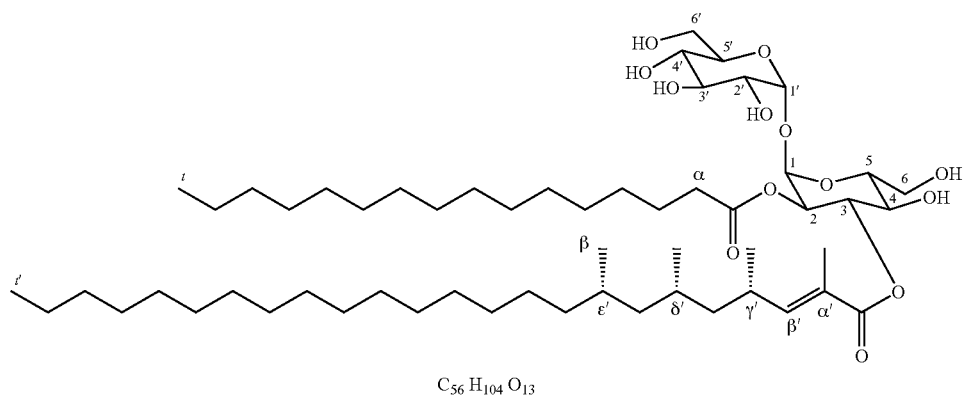

$C_{56}H_{104}O_{13}$

M = 985.3430 g/mol

2-O-Hexadecanoyl-3-O-[(4S,6S,8S)-2,4,6,8-tetramethyltetracos-2-enoyl]-α,α'-D-trehalose RMN $^1$H (250 MHz, CDCl$_3$/MeOD 4/1)

δ=0.77 ppm (t, 3H-t, 3H-t', $^3$J=6.5 Hz); δ=0.7; 0.72 and 0.86 ppm (3d, (CH$_3$)$_{\gamma'}$, (CH$_3$)$_{\delta'}$, (CH$_3$)$_{\delta'}$); δ=1-1.5 ppm (m, H aliphatic); δ=1.73 ppm (d, (CH$_3$)$_{\alpha'}$, $^4$J=1.5 Hz); δ=2.13 ppm (m, 2H-α); δ=2.5 ppm (m, H-γ'); δ=3.2-3.9 ppm (m, H-2', H-3', H-4, H-4', H-5, H-5', 2H-6, 2H-6'); δ=4.84 ppm (dd, H-2, $^3$J$_{2-1}$=4 Hz and $^3$J$_{2-3}$=10 Hz); =5.0 ppm (d, H-1, $^3$J$_{1-2}$=4 Hz); =5.16 ppm (d, H-1', $^3$J$_{1'-2'}$=4 Hz); δ=5.36 ppm (t, H-3, $^3$J$_{3-4}$=$^3$J$_{3-2}$=10 Hz); δ=6.43 ppm (dq, H-β', $^3$J$_{\beta'-\gamma'}$=10.2 Hz, $^4$J=1 Hz).

MALDI-Tof (positive mode): M/Z=1007.61

Compound g:

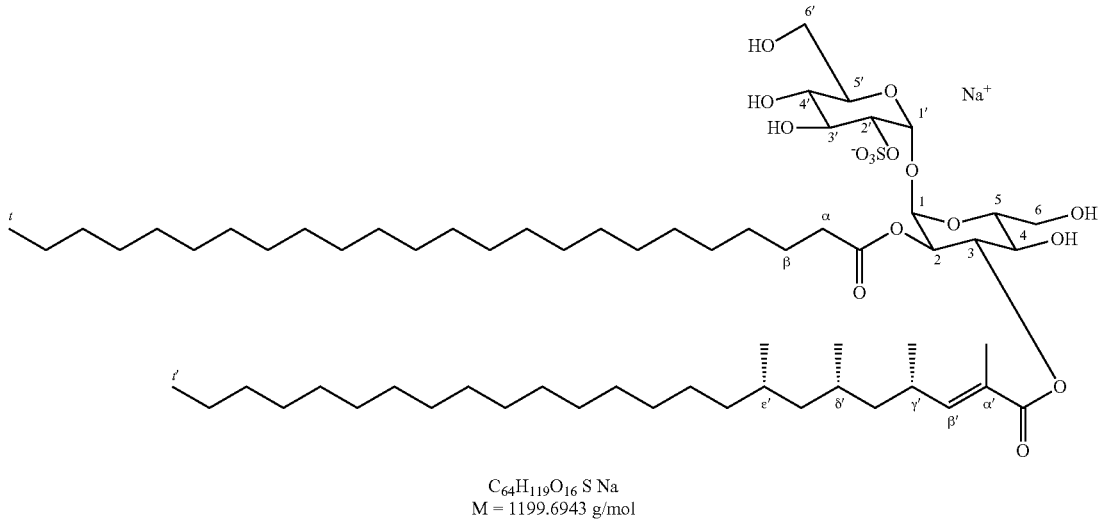

$C_{64}H_{119}O_{16}$ S Na
M = 1199.6943 g/mol

2'-O-Sulfate-2-O-tetracosanoyl-3-O-[(4S,6S,8S)-2,4,6,8-tetramethyltetracos-2-enoyl]-α,α'-D-trehalose RMN $^1$H (250 MHz, CDCl$_3$/MeOD 4/1)

δ=0.6-0.9 ppm (m, 3H-t, 3H-t', (CH$_3$)$_{\gamma'}$, (CH$_3$)$_{\beta'}$, (CH$_3$)$_{\epsilon'}$); δ=1-1.5 ppm (m, H aliphatic); δ=1.73 ppm (d, (CH$_3$)$_{\alpha'}$, $^4$J=1 Hz); δ=2.1 ppm (m, 2H-α); δ=2.5 ppm (m, H-γ'); δ=3.1-4.5 ppm (m, H-2', H-3', H-4, H-4', H-5, H-5', 2H-6, 2H-6'); δ=4.8 ppm (dd, H-2, $^3$J$_{2-1}$=4 Hz and $^3$J$_{2-3}$=10 Hz); δ=5.16 ppm (d, H-1, $^3$J$_{1-2}$=4 Hz); δ=5.3 ppm (t, H-3, $^3$J$_{3-4}$=$^3$J$_{3-2}$=10 Hz); δ=5.46 ppm (d, H-1', $^3$J$_{1'-2'}$=4 Hz) δ=6.43 ppm (dq, $^3$J$_{\beta'-\gamma'}$=10.2 Hz, $^4$J=1 Hz)

MALDI-Tof (negative mode): M/Z=1175.57

Compound h:

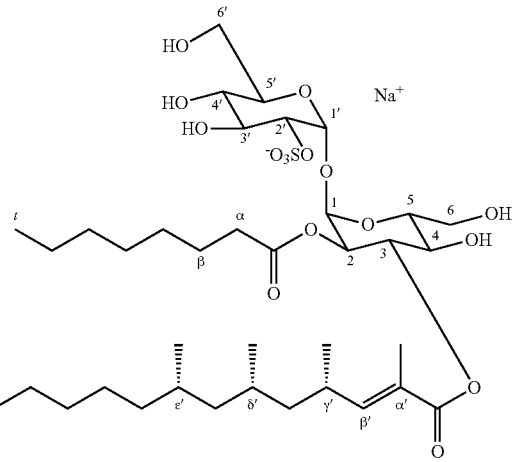

$C_{48}H_{87}O_{16}$ S Na
M = 975.2642 g/mo

2-O-Octanoyl-2'-O-sulfate-3-O-[(4S,6S,8S)-2,4,6,8-tetramethyltetracos-2-enoyl]-α,α'-D-trehalose RMN $^1$H (250 MHz, CDCl$_3$/MeOD 4/1)

δ=0.65 ppm (d, (CH$_3$)$_δ$', $^3$J=7 Hz); δ=0.7 ppm (t, 3H-t, 3H-t', $^3$J=7 Hz); δ=0.8 ppm (d, (CH$_3$)$_γ$'', $^3$J=7 Hz); δ=1.1-1.5 ppm (m, H aliphatic); δ=1.7 ppm (s, (CH$_3$)$_α$'); δ=2.1 ppm (t, 2H-α, $^3$J$_{α-β}$=7 Hz); δ=2.5 ppm (m, H-γ'); δ=3.1-4.5 ppm (m, H-2', H-3', H-4, H-4', H-5, H-5', 2H-6, 2H-6'); δ=4.8 ppm (dd, H-2, $^3$J$_{2-1}$=4 Hz and $^3$J$_{2-3}$=10 Hz); δ=5.15 ppm (d, H-1, $^3$J$_{1-2}$=4 Hz); δ=5.3 ppm (t, H-3, $^3$J$_{3-4}$=$^3$J$_{3-2}$=10 Hz); δ=5.4 ppm (d, H-1', $^3$J$_{1'-2'}$=4 Hz); δ=6.4 ppm (d, H-β', $^3$J$_{β'-γ'}$=10.2 Hz).

MALDI-Tof (negative mode): M/Z=951.43

Compound i:

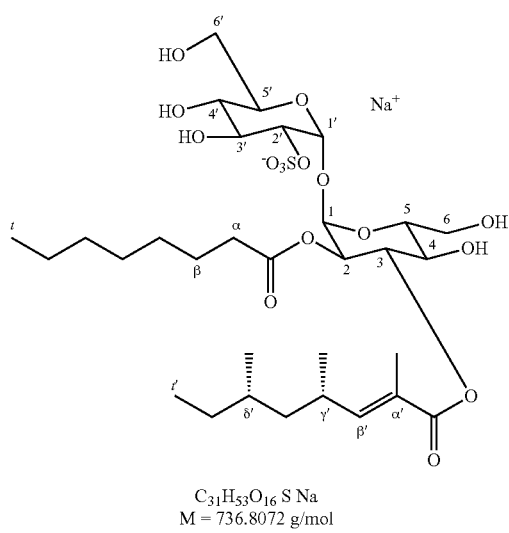

C$_{31}$H$_{53}$O$_{16}$ S Na
M = 736.8072 g/mol

2-O-Octanoyl-2'-O-sulfate-3-O-[(4S,6S)-2,4,6-trimethyloct-2-enoyl]-α,α'-D-trehalose RMN $^1$H (600 MHz, cryoprobe, MeOD)

δ=0.86 ppm (d, (CH$_3$)$_δ$', $^3$J=6.6 Hz); δ=0.88 ppm (t, 3H-t', $^3$J=7.2 Hz); δ=0.9 ppm (t, 3H-t, $^3$J=7.2 Hz); δ=0.99 ppm (d, (CH$_3$)$_γ$'', $^3$J=7.2 Hz); δ=1.1-1.6 ppm (m, H aliphatic); δ=1.85 ppm (d, (CH$_3$)$_α$', $^4$J=1.5 Hz); δ=2.27 and 2.3 ppm (2td, 2H-α, $^3$J$_{α-β}$=7.2 Hz, $^2$J=14.4 Hz); δ=2.66 ppm (m, H-γ'); δ=3.41 ppm (t, H-4', $^3$J$_{4'-3'}$=$^3$J$_{4'-5'}$=9.3 Hz); δ=3.66 ppm (dd, 1H-6', $^3$J$_{6'-5'}$=5.7 and $^2$J=11.7 Hz); δ=3.68 ppm (t, H-4, $^3$J$_{4-5}$=$^3$J$_{4-3}$=10 Hz); δ=3.75 ppm (m, H-5', H-6, H-6'); δ=3.91 ppm (dd, H-6, $^2$J=12 Hz, $^3$J$_{6-5}$=2.4 Hz); δ=3.92 ppm (t, $^3$J$_{3'-2'}$=$^3$J$_{3'-4'}$= 9.3 Hz); δ=4.19 ppm (dd, H-2', $^3$J$_{2'-1}$=3.6 Hz, $^3$J$_{2'-3'}$= 9.3 Hz); δ=4.24 ppm (ddd, H-5, $^3$J$_{5-6}$=2.4 Hz, 3J$_{5-6}$=4.2 Hz, $^3$J$_{5-4}$=10 Hz); δ=4.98 ppm (dd, H-2, $^3$J$_{2-1}$=3.6 Hz and $^3$J$_{2-3}$= 10 Hz); δ=5.27 ppm (d, H-1, $^3$J$_{1-2}$=3.6 Hz); δ=5.50 ppm (d, H-1', $^3$J$_{1'-2}$=3.6 Hz); δ=5.51 ppm (t, H-3, $^3$J$_{3-4}$=$^3$J$_{3-2}$=10 Hz); δ=6.52 ppm (dquad, H-β', $^3$J$_{β'-γ'}$=10.2 Hz, $^4$J=1.5 Hz)

RMN $^{13}$C (600 MHz, cryoprobe, MeOD)

δ=11.6 ppm, C-t'; δ=12.8 ppm, (CH$_3$)$_α$'; δ=14.4 ppm, C-t; δ=19.5 ppm, (CH$_3$)$_δ$'; δ=20.8 ppm, (CH$_3$)$_γ$'; δ=23.7 ppm, C-(t-1); δ=26.0 ppm, C-β; δ=30; 30.1; 32.8 ppm, C octanoic acid; δ=31.1 ppm, C-(t-1)'; δ=32.1 ppm, C-γ'; δ=33.6 ppm, C-δ'; δ=35.0 ppm, C-α; δ=45.3 ppm, C-δ'; δ=61.8 ppm, C-6; δ=62.5 ppm, C-6'; δ=69.9 ppm, C-4; δ=71.6 ppm, C-4'; δ=72.0 ppm, C-2; δ=72.8 ppm, C-3'; δ=73.4 ppm, C-5; δ=74.1 ppm, C-5'; δ=74.4 ppm, C-3; δ=78.4 ppm, C-2'; δ=93.5 ppm, C-1; δ=94.3 ppm, C-1'; δ=127.2 ppm, C-α'; δ=150.2 ppm, C-β'; δ=169.3 ppm, (C=O)$_3$; δ=174.3 ppm, (C=O)$_2$.

MALDI-Tof (negative mode): M/Z=713.15 as well as the following compounds:

Compound j:

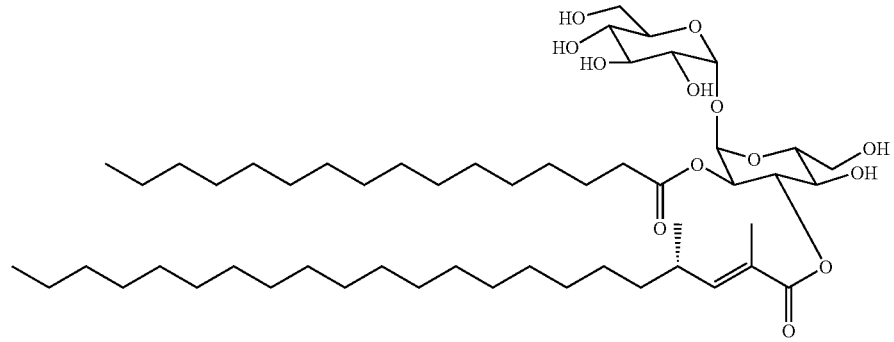

Compound k:
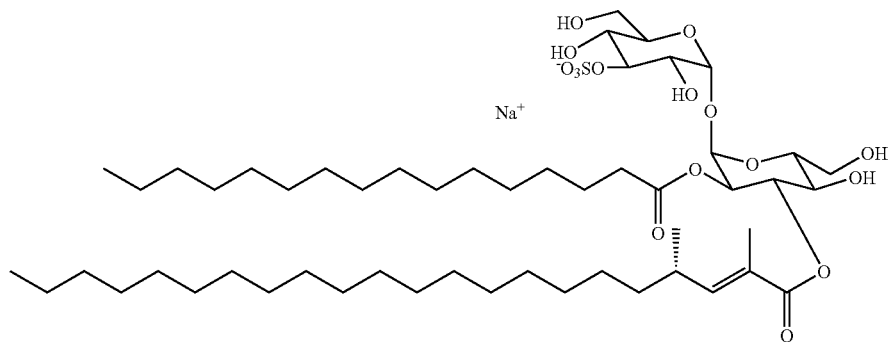
Compound l:
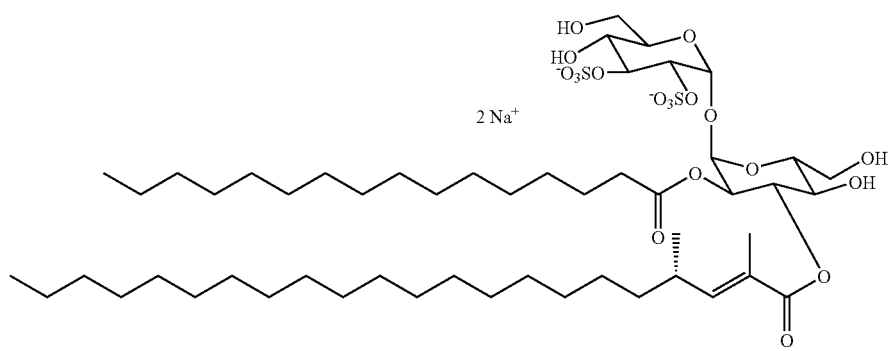
Compound m:
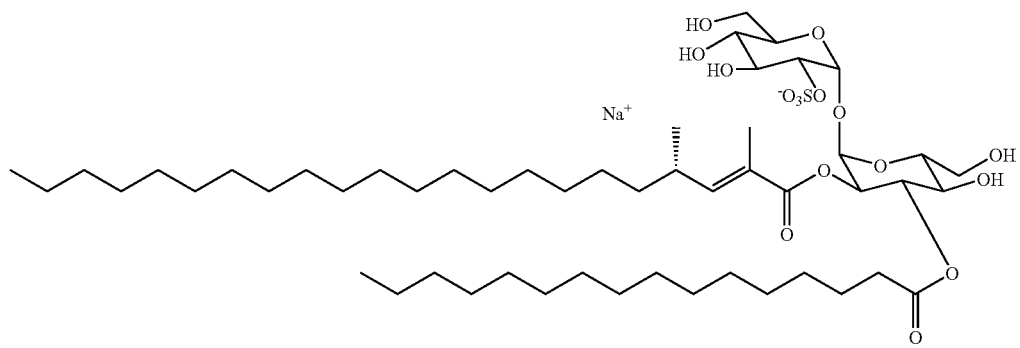
Compound n:
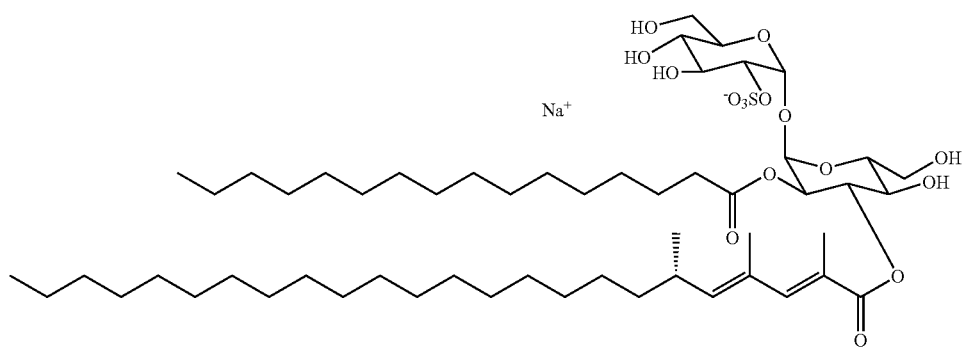

Compound o:

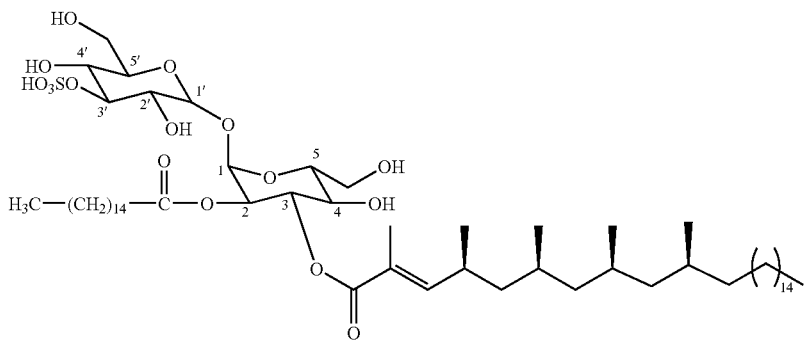

Example 2

Ex Vivo Assay of *Mycobacterium tuberculosis* Sulfoglycolipids

To define the immunogenicity of sulfoglycolipids-antigens, IFN-γ release is measured after stimulation with the purified sulfoglycolipids. $2 \times 10^5$ PBMC per/well are incubated for 4 days in the presence of GM-CSF (500 U/mL) and IL-4 (5 ng/mL). Autologous effector T-cells are incubated in 10% human serum during this time. The sulfoglycolipids (10 μg/mL) are added to the irradiated, CD1-expressing antigen-presenting cells. Finally, effector cells are added ($2 \times 10^5$/well) and IFN-γ release is measured by ELISA in the supernatants after 18 hours. The IFN-γ ELISA is performed in 96-well immunosorbent plates, which are coated with an IFN-γ capture antibody (2 μg/mL) overnight. Non-specific binding sites are blocked with PBS containing 1% bovine serum albumin. The supernatants are diluted 1:1 and added in a final volume of 100 μl. Plates are incubated at room temperature for 2 hours and removed by thorough washing (3-4 times). Finally, a biotinylated anti-IFN-γ antibody is added for 1 hour (2 μg/mL). For detection of immunoreactive IFN-γ, horseradish-peroxidase is added for 30 min. Finally, a chromogenic substrate (TMB, Endogen, MA, USA) is added. After 20 min. incubation, the reaction is stopped by the addition of sulfuric acid (2%). The intensity of the staining is determined photometrically at a wavelength of 480 nm. To estimate the concentration of cytokine in the supernatants, an IFN-γ standard with a known concentration is included in all tests.

Example 3

In Vivo Study

PPD$^+$ donors (positive to the tuberculin test) and PPD$^-$ donors (negative to the tuberculin test) are recruited and administered with a compound of the invention. The response to the sulfoglycolipids is measured by assessing the IFN-γ production with the ELISA test (15 pg/mL) in each patient in each group. The responses in each group are compared.

Example 4

Antigen Presentation Assay

The release of IFN-γ produced by T cell clone Z4B27 prepared in accordance with the method disclosed in WO 2004/092192 in response to stimulation by the compounds of the invention was measured.

CD1+APC were preincubated at $5 \times 10^4$ cells/well for 2 h at 37° C. with sonicated antigen (1-10 μg/mL) before addition of T cells ($5 \times 10^4$/well in triplicate). After 36 h released TNF-α and IFN-γ were measured using sandwich ELISA kits (Instrumentation Laboratory). Data are expressed as mean ng/mL or pg/mL±SD of triplicates. All experiments were repeated at least 2 times.

Results are illustrated in FIG. 1 for compound e (cpd e) of the invention. They evidence that compounds of the invention show better activity than corresponding unsulfated compounds (see compound f "cpd f") and than corresponding saturated compounds as disclosed in WO 2004/092192 on the basis of comparative compound (see "comp".) of formula:

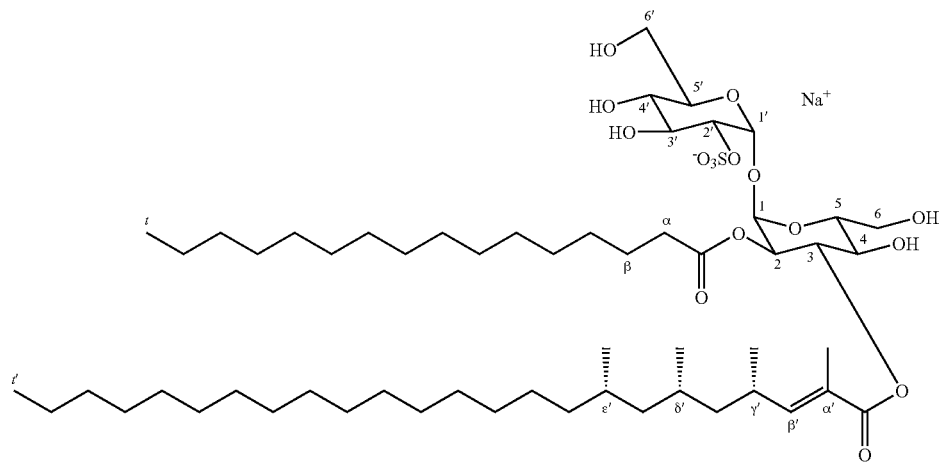

Figure 2:
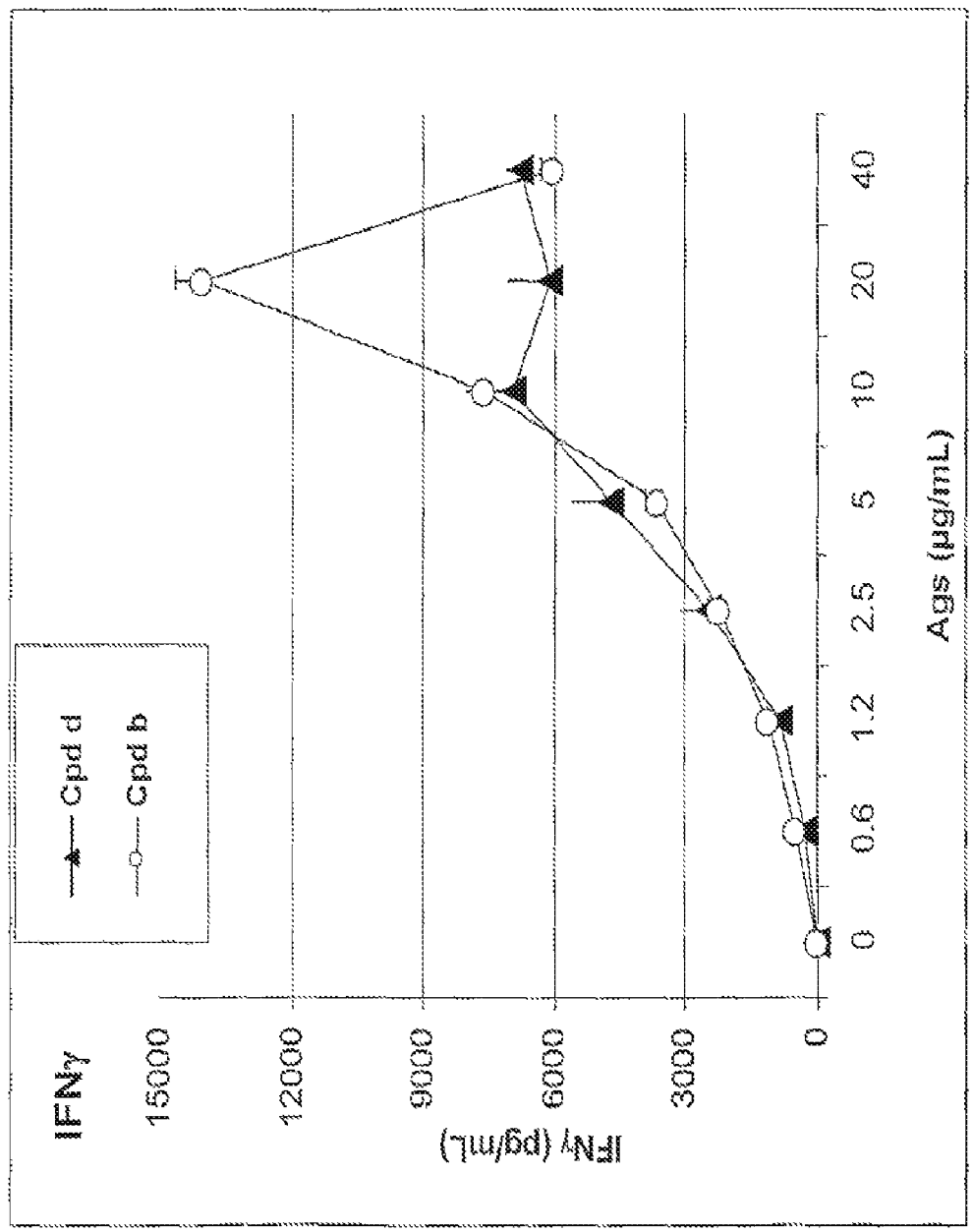

Further results illustrated in FIG. 2 show the activity of compounds b and d (cpd b and cpd d).

The invention claimed is:

1. A compound of general formula (I):

(I)

[chemical structure of disaccharide with HO, HO, R³'O, OR²', R²O, OR³, OH, OH substituents]

wherein:
  $R^{2'}$, $R^{3'}$, identical or different, are independently chosen from H, $SO_3H$ or $SO_3^-/M^+$, provided that at least one of $R^{2'}$, $R^{3'}$ is $SO_3H$ or $SO_3^-/M^+$;
  $M^+$ is the cation of a metal, such as $Na^+$, $K^+$;
  $R^2$, $R^3$, identical or different, are independently chosen from:
  a) fatty acyl groups
  b)

$$-\overset{O}{\underset{\|}{C}}-X,$$

where X is an unsaturated linear or ramified hydrocarbon chain optionally substituted with one or more substituents;
  where at least one of $R^2$, $R^3$ is b);
  and its enantiomers, diastereoisomers, mixtures thereof and pharmaceutically acceptable salts or esters.

2. The compound of formula (I) according to claim 1, wherein $R^{2'}$ is $SO_3H$ or $SO_3^-/M^+$ and $R^{3'}$ is H.

3. The compound according to claim 1 wherein X is of formula (b-1):

$$-CR^i=CR^j-Y \quad (b-1)$$

where:
  Y is a saturated or unsaturated, linear or ramified hydrocarbon chain optionally substituted with one or more substituents;
  $R_i, R_j$, identical or different, are independently chosen from H, Alkyl.

4. The compound according to claim 3, wherein $R^i$ is Methyl and $R^j$ is H.

5. The compound according to claim 3, wherein Y is a saturated linear alkyl chain optionally substituted with one to ten alkyl groups.

6. The compound according to claim 1, wherein the b) chain is of formula (b-2):

(b-2)

[structure: C(=O)–CH=C(T²)–(CH(T^i))_r–(...)_l–(CH_2)_q–CH_3]

where:
  r is an integer chosen from 1, 2 or 3;
  l is an integer chosen from 0 to 10;
  q is an integer chosen from 0 to 50;
  provided that $l+q \geq 1$;
  $T^2$ is an alkyl;
  each $T^i$, identical or different, are independently chosen from alkyl groups.

7. The compound according to claim 6, wherein:
  r is 1;
  l is 1, 2 or 3;
  q is an integer chosen from 10 to 20;
  $T^2$ is a methyl;
  each $T^i$ is methyl, and the carbon atom to which $T^i$ is attached exhibits a (S) configuration.

8. The compound according to claim 1, wherein said fatty acyl groups are selected from the group consisting of:

$$-\overset{O}{\underset{\|}{C}}-(CH_2)_6-CH_3,$$
(octanoyl)

$$-\overset{O}{\underset{\|}{C}}-(CH_2)_{14}-CH_3,$$
(palmitoyl)

$$-\overset{O}{\underset{\|}{C}}-(CH_2)_{16}-CH_3,$$
(stearoyl)

$$-\overset{O}{\underset{\|}{C}}-(CH_2)_{18}-CH_3,$$
(arachidioyl)

$$-\overset{O}{\underset{\|}{C}}-(CH_2)_{20}-CH_3,$$
(docosanoyl)

$$-\overset{O}{\underset{\|}{C}}-(CH_2)_{22}-CH_3,$$
(tetracosanoly)

$$-\overset{O}{\underset{\|}{C}}-\underset{CH_3}{CH}-(CH_2-\underset{CH_3}{CH})_n-\underset{OH}{CH}-(CH_2)_m-CH_3, \text{ and}$$
(hydroxyphthioceranoyl)

$$-\overset{O}{\underset{\|}{C}}-\underset{CH_3}{CH}-(CH_2-\underset{CH_3}{CH})_n-CH_2-(CH_2)_m-CH_3,$$
(phthioceranoyl)

wherein m is 14 or 16 and n is an integer from 2 to 10, and $$-\overset{O}{\underset{\|}{C}}-\underset{CH_3}{CH}-(CH_2-\underset{CH_3}{CH})_n-CH_2-(CH_2)_m-CH_3,$$
(phthioceranoyl)

wherein m is 14 or 16 and n is an integer from 2 to 10.

9. The compound according to claim 1, wherein $R^2$ is a) fatty acyl group and $R^3$ is b)

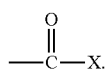

10. The compound according to claim 1 of formula (II):

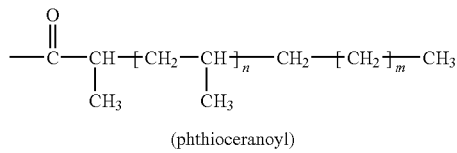

(phthioceranoyl)

where $R^{2'}$, $R^{3'}$, r, p, l, q, $T^2$, $T^i$ are defined as above, or the corresponding salt thereof;
and its enantiomers, diastereoisomers, mixtures thereof and pharmaceutically acceptable salts.

11. The compound according to claim 10, wherein:
l=1, q=14 and r=1;
l=2, q=14 and r=1;
l=3, q=14 and r=1;
l=4, q=14 and r=1;
l=1, q=14 and r=2;
l=2, q=14 and r=2;
l=3, q=14 and r=2;
l=4, q=14 and r=2;
l=1, q=12 and r=1;
l=2, q=12 and r=1;
l=3, q=12 and r=1;
l=4, q=12 and r=1;
l=1, q=12 and r=2;
l=2, q=12 and r=2;
l=3, q=12 and r=2;
l=4, q=12 and r=2;
l=1, q=16 and r=1;
l=2, q=16 and r=1;
l=3, q=16 and r=1;
l=4, q=16 and r=1;
l=1, q=16 and r=2;
l=2, q=16 and r=2;
l=3, q=16 and r=2; or
l=4, q=16 and r=2; and
where p is 6 to 22 and $T^2$ and $T^i$ are methyl.

12. The compound according to claim 1 selected from the group consisting of:

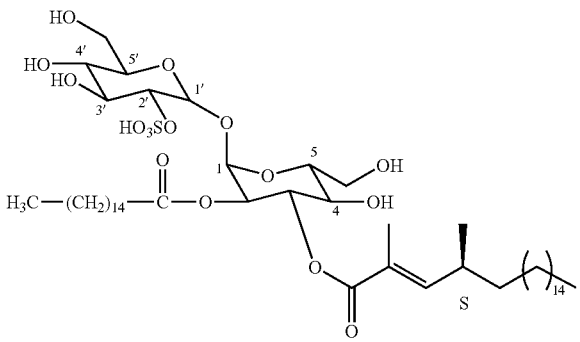

(II.1)

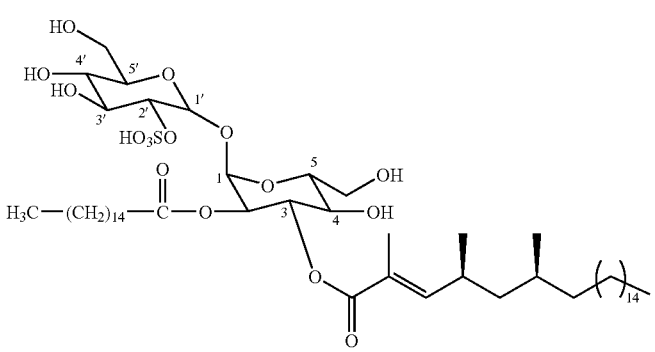

(II.2)

-continued
(II.3)
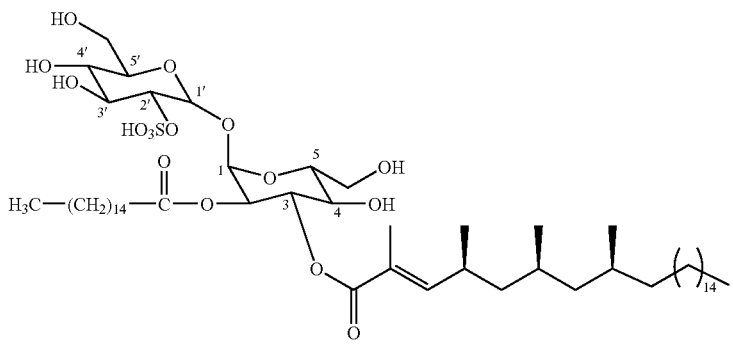
(II.4)
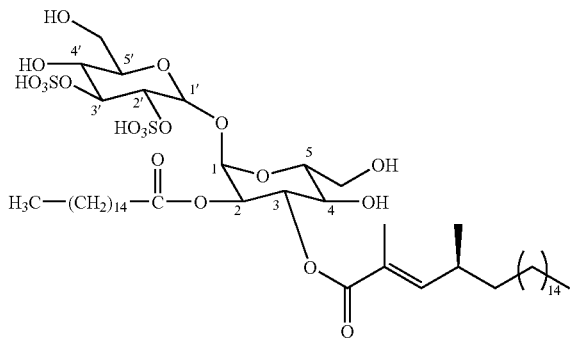
(II.5)
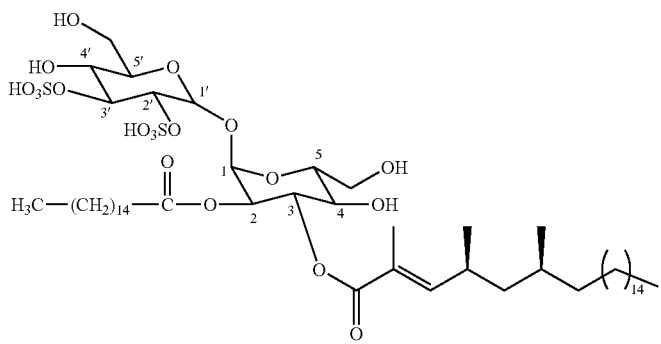
(II.6)
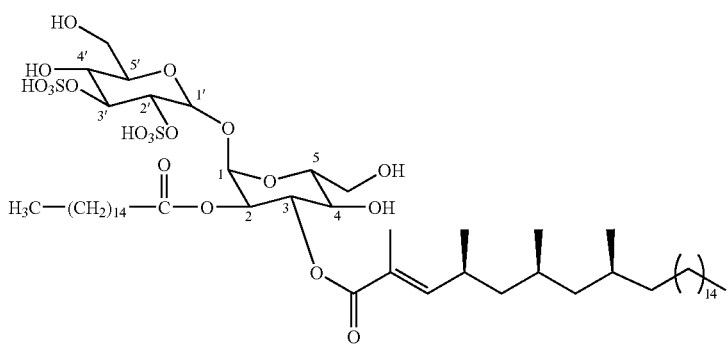

and their corresponding salts, and its enantiomers, diastereoisomers, mixtures thereof and pharmaceutically acceptable salts.

13. A pharmaceutical composition comprising at least one compound as defined in claim 1 in association with a pharmaceutically acceptable vehicle.

14. The pharmaceutical composition according to claim 13 in a form intended for administration by oral or injectable route.

15. The pharmaceutical composition according to claim 13, which is immunogenic, further comprising one or more products selected from the group consisting of cytokines, DNA fragments encoding *M. tuberculosis* antigens, live *M. tuberculosis* deletion mutants and live recombinant *Bacillus* of Calmette and Guérin.

16. An immunogenic product comprising:
at least one compound according to claim 1, and
at least one product selected from the group consisting of cytokines, DNA fragments encoding *M. tuberculosis* antigens, live *M. tuberculosis* deletion mutants and live recombinant *Bacillus* of Calmette and Guérin, as a combined preparation for simultaneous, separate or sequential administration with said at least one compound.

17. A method for the treatment of tuberculosis comprising the administration of at least one compound according to claim 1.

18. A kit for diagnosing tuberculosis comprising:
a compound of formula (X):

<chemical structure of formula (X) showing a disaccharide with HO, HO, R³'O, R²'O substituents on one sugar ring linked via O to another sugar ring with R²O, OR³, OH, OH substituents> where
$R^{2'}$, $R^{3'}$, identical or different, are independently chosen from H, $SO_3H$ or $SO_3^-H/M^+$, provided that at least one of $R^{2'}$, $R^{3'}$ is $SO_3H$ or $SO_3^-/M^+$; $M^+$ is the cation of a metal, such as $Na^+$, $K^+$;

$R^2$, $R^3$, identical or different, are independently chosen from:
a) fatty acyl groups
b)

$$-C(=O)-X,$$

where X is an unsaturated linear or ramified hydrocarbon chain optionally substituted with one or more substituents;

and its enantiomers, diastereoisomers, mixtures thereof and pharmaceutically acceptable salts or esters,
dendritic cells; and
means for detecting T lymphocytes activation.

* * * * *